(12) United States Patent
Browning

(10) Patent No.: US 8,821,369 B2
(45) Date of Patent: *Sep. 2, 2014

(54) METHOD FOR SOFT TISSUE ANCHORING WITH INTRODUCER

(75) Inventor: James Browning, Glasgow (GB)

(73) Assignee: Colorplast A/S, Humlebaek (DK)

(*) Notice: Subject to any disclaimer, the term of this patent is extended or adjusted under 35 U.S.C. 154(b) by 599 days.

This patent is subject to a terminal disclaimer.

(21) Appl. No.: 13/149,987

(22) Filed: Jun. 1, 2011

(65) Prior Publication Data

US 2011/0230705 A1    Sep. 22, 2011

Related U.S. Application Data

(63) Continuation of application No. 12/837,601, filed on Jul. 16, 2010, now Pat. No. 8,007,430, which is a continuation of application No. 11/199,061, filed on Aug. 8, 2005, now Pat. No. 7,789,821, which is a continuation of application No. 10/398,992, filed as application No. PCT/GB01/04554 on Oct. 12, 2001, now Pat. No. 6,960,160.

(30) Foreign Application Priority Data

Oct. 12, 2000 (GB) .................................. 0025068.8

(51) Int. Cl.
*A61F 2/00* (2006.01)
*A61B 19/00* (2006.01)
*A61B 17/06* (2006.01)
*A61B 17/04* (2006.01)
*A61B 17/00* (2006.01)

(52) U.S. Cl.
CPC ............. *A61F 2/0063* (2013.01); *A61F 2/0045* (2013.01); *A61B 2017/0464* (2013.01); *A61B 2017/0435* (2013.01); *A61B 2017/0412* (2013.01); *A61B 2017/0414* (2013.01); *A61B 2017/0427* (2013.01); *A61B 2017/0409* (2013.01); *A61B 2017/00805* (2013.01); *A61B 2017/0417* (2013.01); *A61B 17/06109* (2013.01); *A61B 17/0401* (2013.01)
USPC ............................................. 600/30; 600/37

(58) Field of Classification Search
USPC ......... 600/29–32, 37; 128/DIG. 25, 897–898; 606/139–144, 151–158, 232–233
See application file for complete search history.

(56) References Cited

U.S. PATENT DOCUMENTS

| 2,738,790 A | 3/1956 | Todt, Sr. et al. |
| 3,054,406 A | 9/1962 | Usher |

(Continued)

FOREIGN PATENT DOCUMENTS

| DE | 2305815 A1 | 8/1974 |
| DE | 4220283 A1 | 12/1993 |

(Continued)

OTHER PUBLICATIONS

Spinosa, JP et al., Transobturator surgery for female stress incontinence: a comparative anatomical study of outside-in vs. inside-out techniques, BJU Intl., 100(5), pp. 1097-1102 (Nov. 2007).

(Continued)

*Primary Examiner* — John Lacyk
(74) *Attorney, Agent, or Firm* — Colorplast Corp., Colorplast A/S; Nick Baumann

(57) ABSTRACT

A method of providing support to an anatomical structure of the pelvis includes making a vaginal incision for providing access for placement of a mesh support device below a urethra of a patient without penetrating an abdominal wall of the patient. The mesh support device includes a sling portion and first and second soft tissues connected to first and second ends of the sling portion. The mesh support device is delivered through the vaginal incision using an introducer including a curved elongate shaft having a distal portion and a proximal portion connected to a handle. A suture is passed through a hollow tubular section of the first soft tissue anchor. The suture passed through an aperture in a distal end of the introducer and the introducer is advanced over the suture until the first soft tissue anchor is located at the distal end of the introducer.

13 Claims, 16 Drawing Sheets

(56) References Cited

U.S. PATENT DOCUMENTS

Figure 1:
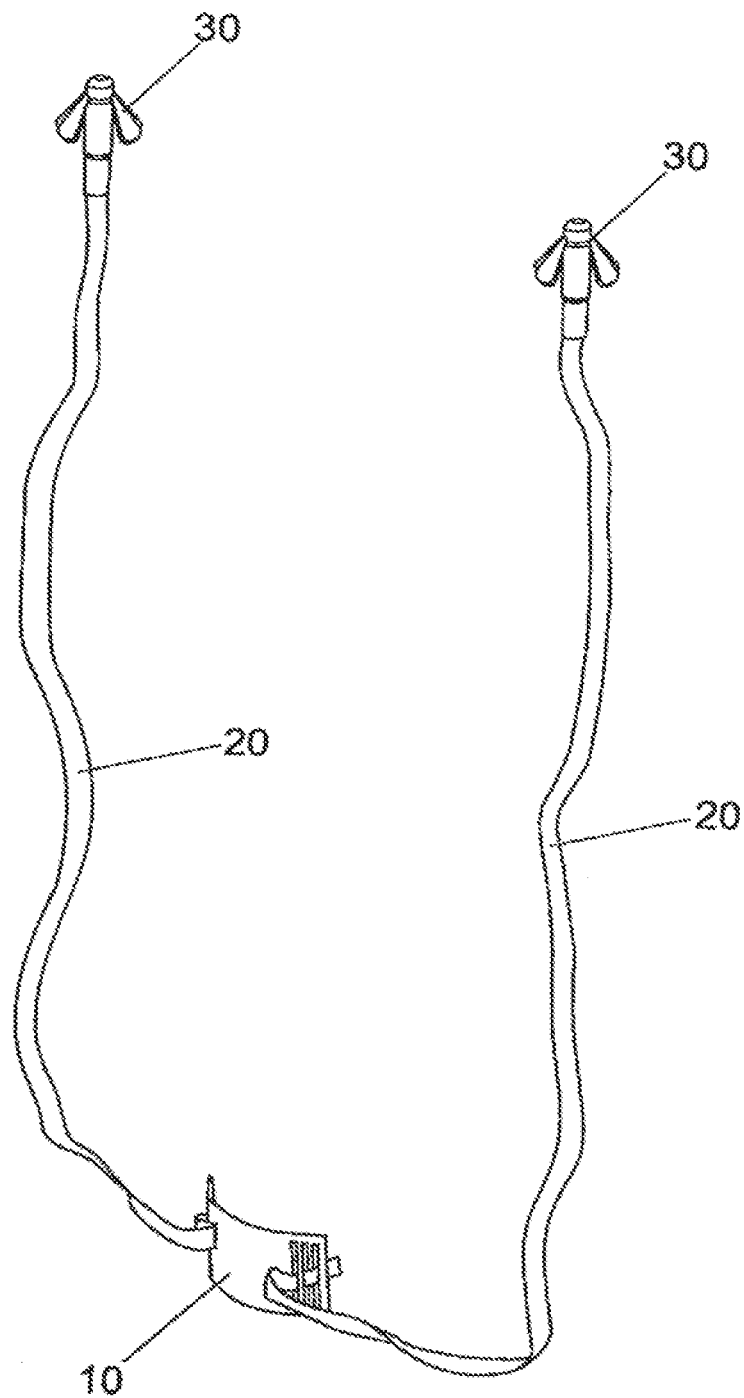

| | | |
|---|---|---|
| 3,124,136 A | 3/1964 | Usher |
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,441,497 A | 4/1984 | Paudler |
| 4,444,933 A | 4/1984 | Columbus et al. |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,938,760 A | 7/1990 | Burton et al. |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,250,033 A | 10/1993 | Evans et al. |
| 5,256,133 A | 10/1993 | Spitz |
| 5,259,835 A | 11/1993 | Clark et al. |
| 5,281,237 A | 1/1994 | Gimpelson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,645,568 A | 7/1997 | Chervitz et al. |
| 5,647,836 A | 7/1997 | Blake, III et al. |
| 5,669,935 A | 9/1997 | Rosenman et al. |
| 5,683,349 A | 11/1997 | Makower et al. |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,807,403 A | 9/1998 | Beyar et al. |
| 5,816,258 A | 10/1998 | Jervis |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,988,171 A | 11/1999 | Sohn et al. |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil Vernet |
| 6,159,207 A | 12/2000 | Yoon |
| 6,162,962 A | 12/2000 | Hinsch et al. |
| 6,168,611 B1 | 1/2001 | Rizvi |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |

(56) References Cited

U.S. PATENT DOCUMENTS

| | | | |
|---|---|---|---|
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner et al. |
| 6,544,273 B1 | 4/2003 | Harari et al. |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Gellman |
| 6,786,861 B1 | 9/2004 | Pretorius |
| 6,830,052 B2 | 12/2004 | Carter et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,960,160 B2 | 11/2005 | Browning |
| 7,025,063 B2 | 4/2006 | Snitkin et al. |
| 7,070,556 B2 | 7/2006 | Anderson et al. |
| 7,070,558 B2 | 7/2006 | Gellman et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,140,956 B1 | 11/2006 | Korovin et al. |
| 7,156,858 B2 | 1/2007 | Schuldt Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,387,634 B2 | 6/2008 | Benderev |
| 7,395,822 B1 | 7/2008 | Burton et al. |
| 7,410,460 B2 | 8/2008 | Benderev |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 | 7/2011 | Browning |
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Romero Maroto |
| 8,047,983 B2 | 11/2011 | Browning |
| 8,092,366 B2 | 1/2012 | Evans |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,162,818 B2 | 4/2012 | Browning |
| 8,167,785 B2 | 5/2012 | Browning |
| 8,182,412 B2 | 5/2012 | Browning |
| 8,182,413 B2 | 5/2012 | Browning |
| 8,215,310 B2 | 7/2012 | Browning |
| 8,273,011 B2 | 9/2012 | Browning |
| 8,449,450 B2 | 5/2013 | Browning |
| 8,454,492 B2 | 6/2013 | Browning |
| 8,469,877 B2 | 6/2013 | Browning |
| 8,512,223 B2 | 8/2013 | Browning |
| 8,574,148 B2 * | 11/2013 | Browning ................ 600/30 |
| 8,668,635 B2 | 3/2014 | Browning |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2003/0004395 A1 | 1/2003 | Therin |

(56) References Cited

U.S. PATENT DOCUMENTS

| | | |
|---|---|---|
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 6/2004 | Benderev |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0080317 A1 | 4/2005 | Merade |
| 2005/0107805 A1 | 5/2005 | Bouffier et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0167518 A1 | 7/2008 | Burton et al. |
| 2008/0196729 A1 | 8/2008 | Browning |
| 2008/0200751 A1 | 8/2008 | Browning |
| 2009/0123522 A1 | 5/2009 | Browning |
| 2009/0137862 A1 | 5/2009 | Evans et al. |
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi et al. |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230708 A1 | 9/2011 | Browning |
| 2011/0230709 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237876 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2012/0143000 A1 | 6/2012 | Browning |
| 2012/0149977 A1 | 6/2012 | Browning |
| 2012/0199133 A1 | 8/2012 | Browning |
| 2014/0039244 A1 | 2/2014 | Browning, James |
| 2014/0039247 A1 | 2/2014 | Browning, James |
| 2014/0039248 A1 | 2/2014 | Browning, James |
| 2014/0051917 A1 | 2/2014 | Browning, James |

FOREIGN PATENT DOCUMENTS

| | | |
|---|---|---|
| DE | 4304353 A1 | 4/1994 |
| DE | 10019604 C2 | 6/2002 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0139286 B1 | 8/1991 |
| EP | 0470308 A1 | 2/1992 |
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 1093758 A1 | 4/2001 |
| EP | 0719527 B1 | 8/2001 |
| EP | 0643945 B1 | 3/2002 |
| EP | 1060714 B1 | 8/2006 |
| EP | 1274370 B1 | 9/2006 |
| EP | 1296614 B1 | 9/2006 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| RU | 2187251 C1 | 8/2002 |
| RU | 2196518 C2 | 1/2003 |
| SU | 1225547 A1 | 4/1986 |
| SU | 1342486 A1 | 10/1987 |
| SU | 1475607 A1 | 4/1989 |
| WO | WO9100714 A1 | 1/1991 |
| WO | WO9317635 A1 | 9/1993 |
| WO | WO9319678 A2 | 10/1993 |
| WO | WO9533454 A1 | 12/1995 |
| WO | WO9603091 A1 | 2/1996 |
| WO | WO9606567 A1 | 3/1996 |
| WO | WO9713465 A1 | 4/1997 |
| WO | WO9722310 A2 | 6/1997 |
| WO | WO9743982 A1 | 11/1997 |
| WO | WO9819606 A1 | 5/1998 |
| WO | WO9835606 A2 | 8/1998 |
| WO | WO9835616 A1 | 8/1998 |

(56) References Cited

FOREIGN PATENT DOCUMENTS

| | | |
|---|---|---|
| WO | WO9835632 A1 | 8/1998 |
| WO | WO9857590 A1 | 12/1998 |
| WO | WO9916381 A1 | 4/1999 |
| WO | WO9952450 A1 | 10/1999 |
| WO | WO9959477 A1 | 11/1999 |
| WO | WO0007520 A1 | 2/2000 |
| WO | WO0013601 A1 | 3/2000 |
| WO | WO0015141 A1 | 3/2000 |
| WO | WO0018319 A1 | 4/2000 |
| WO | WO0038784 A1 | 7/2000 |
| WO | WO0057812 A1 | 10/2000 |
| WO | WO0064370 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145589 A1 | 6/2001 |
| WO | WO0152729 A2 | 7/2001 |
| WO | WO0156499 A1 | 8/2001 |
| WO | WO0180773 A1 | 11/2001 |
| WO | WO0202031 A1 | 1/2002 |
| WO | WO0226108 A2 | 4/2002 |
| WO | WO0228312 A1 | 4/2002 |
| WO | WO0230293 A1 | 4/2002 |
| WO | WO0232284 A2 | 4/2002 |
| WO | WO0232346 A1 | 4/2002 |
| WO | WO0234124 A2 | 5/2002 |
| WO | WO0239890 A2 | 5/2002 |
| WO | WO02060371 A1 | 8/2002 |
| WO | WO02065921 A1 | 8/2002 |
| WO | WO02065944 A1 | 8/2002 |
| WO | WO02069781 A2 | 9/2002 |
| WO | WO02071953 A2 | 9/2002 |
| WO | WO02078548 A1 | 10/2002 |
| WO | WO02078552 A1 | 10/2002 |
| WO | WO02078568 A1 | 10/2002 |
| WO | WO02078571 A2 | 10/2002 |
| WO | WO02098340 A1 | 12/2002 |
| WO | WO03002027 A1 | 1/2003 |
| WO | WO03013392 A1 | 2/2003 |
| WO | WO03057074 A2 | 7/2003 |
| WO | WO03022260 B1 | 10/2003 |
| WO | WO03086205 A2 | 10/2003 |
| WO | WO03092546 A2 | 11/2003 |
| WO | WO03094781 A1 | 11/2003 |
| WO | WO2004002370 A1 | 1/2004 |
| WO | WO2004002379 A1 | 1/2004 |
| WO | WO2004004600 A1 | 1/2004 |
| WO | WO2004012626 A1 | 2/2004 |
| WO | WO2004098461 A2 | 11/2004 |
| WO | WO2005018494 A1 | 3/2005 |
| WO | WO2005112842 A1 | 12/2005 |
| WO | WO2006015031 A2 | 2/2006 |
| WO | WO2006015042 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Stamey, "Endoscopic Suspension of the Vesical Neck for Urinary Incontinence in Females," Annals of Surgery, 1980, 192(4):465-471.
Stanton, "Suprapubic Approaches for Stress Incontinence in Women," J. Am. Geriatrics Soc., 1990, 38(3):348-351.
Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Ulmsten and Petros, "Intravaginal Slingplasty (IVS): An Ambulatory Surgical Procedure for Treatment of Female Urinary Incontinence," Scand. J. Urol. Nephrol., 1995, 29:75-82.
Ulmsten et al., "A three-year follow up of tension free vaginal tape for surgical treatment of female stress urinary incontinence," Br. J. Obstet. Gynecol., 1999, 106:345-350.
Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 10/106,086, filed Mar. 25, 2002.
U.S. Appl. No. 11/199,061, filed Aug. 8, 2005.
U.S. Appl. No. 60/279,794, filed Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,806, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990, 144:670-673.
Weidemann, Small Intestinal Submucosa for Pubourethral Sling Suspension for the Treatment of Stress Incontinence: First Histopathological Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.
Written Opinion for PCT/GB2009/050174, dated Jun. 24, 2009.
Written Opionion issued in PCT/GB2007/002589, mailed Jan. 22, 2008, 5 pages.
Zacharin and Hamilton, "Pulsion Enterocele: Long-Term Results of an Abdominoperineal Technique," Obstet. Gynecol., 1980, 55(2):141-148.
Zacharin, "The suspensory mechanism of the female urethra," J. Anat., 1963, 97(3):423-427.
International Preliminary Examination Report issued in PCT/GB01/04554, completed Nov. 22, 2002, 6 pages.
International Search Report issued in PCT/GB01/04554, mailed Jan. 29, 2002, 3 pages.
U.S. Appl. No. 13/149,994, filed Jun. 1, 2011.
International Search Report issued in PCT/GB2007/002589, mailed Jan. 22, 2008, 5 pages.
Jacquetin. Utilisation du "TVT" dans la chirurgie . . . J. Gynecol. Obstet. Biol. Reprod. 29: 242-47 (2000).
Jeffcoate, "The Results of the Aldridge Sling Operation for Stress Incontinence," The Journal of Obstetrics and Gynaecology of the British Empire, 1956, 63:36-39.
Jeter, "The Social Impact of Urinary Incontinence," Female Urology, Raz (ed.), W. B. Saunders Company, 1996, Chapter 7, pp. 80-86.
Karram and Bhatia, "Patch Procedure: Modified Transvaginal Fascia Lata Sling for Recurrent or Severe Stress Urinary Incontinence," Obstet Gynecol., 1990, 75:461-463.
Kerdiles et al., "Bypass via the Obturator Foramen in Reconstructive Arterial Surgery of the Lower Extremities," Ann. Chir. Thorac. Cardio-Vasc., 1974, 13(4):335-341.

(56) References Cited

OTHER PUBLICATIONS

Kerr and Staskin, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Klinge et al., "Functional and Morphological Evaluation of a Low-Weight, Monofilament Polypropylene Mesh for Hernia Repair," Journal of Biomedical Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U. et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.
Klutke et al., "Transvaginal Bladder Neck Suspension to Cooper's Ligament: A Modified Pereyra Procedure," Obstet. Gynecol., 1996, 88:294-297.
Korda et al., "Experience with Silastic Slings for Female Urinary Incontinence," Aust. NZ J. Obstet. Gynaecol., 1989, 29:150-154.
Kovac and Cruikshank, "Pubic Bone Suburethral Stabilization Sling for Recurrent Urinary Incontinence," Obstet. Gynecol., 1997, 89:624-627.
Kovac and Cruikshank, "Pubic bone suburethral stabilization sling: a long-term cure for SUI?" Contemporary OB/GYN, 1998, 43(2):51-72.
Kovac, "Follow-up of the Pubic Bone Suburethral Stabilization Sling Operation for Recurrent Urinary Incontinence (Kovac Procedure)," J. Pelvic Surgery, 1999, 5(3):156-160.
Lazarevski, M.B., Suburethral Duplication of the Vaginal Wall—An Original Operation for Urinary Stress Incontinence in Women, 6 Int'l Urogynecol. J. 73-79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Lichtenstein et al., "The Tension-Free Hernioplasty," Am. J. Surgery, 1989, 157:188-193.
Lipton, S. and Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.
Mahoney and Whelan, "Use of Obturator Foramen in Iliofemoral Artery Grafting: Case Reports," Annals of Surgery, 1966, 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at the University of Michigan," J. Urol., 1987, 138:525-526.
McGuire, "Abdominal Procedures for Stress Incontinence," Urologic Clinics of North America, 1985, 12(2):285-290.
McIndoe et al., "The Aldridge Sling Procedure in the Treatment of Urinary Stress Incontinence," Aust. NZ J. Obstet. Gynaecol., 1987, 27:238-239.
McKiel, Jr. et al., "Marshall-Marchetti Procedure: Modification," J. Urol., 1966, 96:737-739.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," The Journal of Obstetrics and Gynaecology of the British Commonwealth, 1968, 75(1):1-9.
Monseur, J., Anatomie Chirurgicale: Les Ligaments Du Perinee Feminin, Sep. 4, 2008.
Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-181.
Morgan et al., "The Marlex sling operation for the treatment of recurrent stress urinary incontinence: A 16-year review," Am. J. Obstet. Gynecol., 1985, 151:224-226.
Morgan, "A sling operation, using Marlex polypropylene mesh, for treatment of recurrent stress incontinence," Am. J. Obstet. Gynecol., 1970, 106(3):369-376.
Narik and Palmrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41(1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10(3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).
Aldridge, "Transplantation of Fascia for Relief of Urinary Stress Incontinence," Am. J. Obstet. Gynecol., 1942, 44:398-411.
Araki et al., "The Loop-Loosening Procedure for Urination Difficulties After Stamey Suspension of the Vesical Neck," J. Urol., 1990, 144:319-323.
Asmussen and Ulmsten, "Simultaneous Urethro-Cystometry with a New Technique," Scand. J. Urol. Nephrol., 1976, 10:7-11.
Beck and McCormick, "Treatment of Urinary Stress Incontinence with Anterior Colporrhaphy," Obstetrics and Gynecology, 1982, 59(3):271-274.
Benderev, "A Modified Percutaneous Outpatient Bladder Neck Suspension System," J. Urol., 1994, 152:2316-2320.
Benderev, "Anchor Fixation and Other Modifications of Endoscopic Bladder Neck Suspension," Urology, 1992, 40(5):409-418.
Bergman and Elia, "Three surgical procedures for genuine stress incontinence: Five-year follow-up of a prospective randomized study," Am. J. Obstet. Gynecol., 1995, 173:66-71.
BioArc SP Sling Kit, www.AmericanMedicalSystems.com, 2006.
Blaivas and Jacobs, "Pubovaginal Fascial Sling for the Treatment of Complicated Stress Urinary Incontinence," J. Urol., 1991, 145:1214-1218.

(56) References Cited

OTHER PUBLICATIONS

Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.
Botros, Cystocele and Rectocele Repair: More Success With Mesh? Jun. 2006.
Bryans, "Marlex gauze hammock sling operation with Cooper's ligament attachment in the management of recurrent urinary stress incontinence," Am. J. Obstet. Gynecol., 1979, 133(3):292-294.
Burch, "Urethrovaginal fixation to Cooper's ligament for correction of stress incontinence, cystocele, and prolapse," Am. J. Obstet. Gynecol., 1961, 81(2):281-290.
Certified priority document for GB Application No. 0025068.8, filed Oct. 12, 2000, 38 pages.
Certified priority document for GB Application No. 0208359.0, filed Apr. 11, 2002, 50 pages.
Certified priority document for GB Application No. 0411360.1, filed May 21, 2004, 31 pages.
Chen, Biologic Grafts and Synthetic Meshes in Pelvic Reconstructive Surgery, Jun. 2007.
Choe and Staskin, "Gore-Tex Patch Sling: 7 Years Later," Urology, 1999, 54:641-646.
Chopra et al., "Technique of Rectangular Fascial Sling," Female Urology, 1996, Raz (ed.), W.B. Saunders Company, Chapter 34, pp. 392-394.
Dargent, D. et al., Pose d'un ruban sous uretral oblique par voie obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].
Das and Palmer, "Laparoscopic Colpo-Suspension," J. Urol., 1995, 154:1119-1121.
de Leval, J., "Novel Surgical Technique for the Treatment of Female Stress Urinary Continence: Transobturator Vaginal Tape Inside-Out," European Urology, 2003, 44:724-730.
DeBord, James R., (1998), "The Historical Development of Prosthetics in Hernia Surgery," Surgical Clinics of North America, 78(6): 973-1006.
Decter, "Use of the Fascial Sling for Neurogenic Incontinence: Lessons Learned," J. Urol., 1993, 150:683-686.
Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].
deTayrac, et al. Prolapse repair by vaginal route using . . . Int. Urogynecol. J. (published online May 13, 2006).
Dwyer, Transvaginal repair of anterior and posterior compartment prolapse with Atrium polypropylene mesh, BJOG: An International Journal of Obstetrics & Gynaecology, Aug. 2004.
Enzelsberger et al., "Urodynamic and Radiologic Parameters Before and After Loop Surgery for Recurrent Urinary Stress Incontinence," Acta Obstet. Gynecol. Scand., 1990, 69:51-54.
Eriksen et al., "Long-Term Effectiveness of the Burch Colposuspension in Female Urinary Stress Incontinence," Acta Obstet. Gynecol. Scand., 1990, 69:45-50.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol., 1987, 138:568-570.
Gruss, "The Obturator Bypass. Indications. Techniques. Outcomes," Chirurgie, 1971, 97:220-226.
Guida and Moore, "The Surgeon At Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report," Obstet. Gynecol., 1996, 88:1045-1049.
Hardiman, et al. Cystocele repair using polypropylene mesh. Br. J. Obstet. Gynaecol. 107: 825-26 (2000).
Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Hohenfellner and Petri, "Sling Procedures," Surgery of Female Incontinence, 2nd edition, SpringerVeriag, pp. 105-113.
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics—Theory and Practice, 1996, Williams & Wilkins, pp. 569-579.
Ingelman-Sundberg and Ulmsten, "Surgical Treatment of Female Urinary Stress Incontinence," Contr. Gynec. Obstet., 1983, 10:51-69.
International Search Report for PCT/GB2009/050174, dated Jun. 24, 2009.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," OBG Management, 2003, pp. 17-37.
Pelosi III and Pelosi, "Pubic Bone Suburethral Stabilization Sling: Laparoscopic Assessment of a Transvaginal Operation for the Treatment of Stress Urinary Incontinence," Journal of Laparoendoscopic & Advanced Surgical Techniques, 1999, 9(1):45-50.
Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the midurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol. Scand., 1992, 71:529-536.
Petros and Ulmsten, "An Anatomical Basis for Success and Failure of Female Incontinence Surgery," Scand. J. Urol. Nephrol., 1993, (Suppl. 3):55-60.
Petros and Ulmsten, "An Integral Theory and Its Method for the Diagnosis and Management of Female Urinary Incontinence," 153 Scand. J. Urol. Nephrol. 1, 64 (1993).
Petros and Ulmsten, "An Integral Theory of Female Urinary Incontinence," Acta Obstet. Gynecol. Scand., 1990, 69 (Suppl. 153):7-31.
Petros and Ulmsten, "Bladder Instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet. Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., 1993, Suppl. 153:69-71.

(56) References Cited

OTHER PUBLICATIONS

Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.

Petros and Ulmsten, "Part I: Theoretical, Morphological, Radiographical Correlations and Clinical Perspective," Scand. J. Urol. Nephrol., 1993, Suppl. 153:5-28.

Petros and Ulmsten, "Part II: The Biomechanics of Vaginal Tissue and supporting Ligaments with Special Relevance to the Pathogenesis of Female Urinary Incontinence," Scand. J. Urol. Nephrol., 1993, Suppl. 153:29-40.

Petros and Ulmsten, "Part III: Surgical Principles Deriving from the Theory," Scand. J. Urol. Nephrol., 1993, Suppl. 153:41-52.

Petros and Ulmsten, "Part IV: Surgical Applications of the Theory—Development of the Intravaginal Sling Plasty (IVS) Procedure," Scand. J. Urol. Nephrol., 1993, Suppl. 153:53-54.

Petros and Ulmsten, "Pinch Test for Diagnosis of Stress Urinary Incontinence," Acta Obstet. Gynecol. Scand., 1990, 69(Suppl. 153):33-35.

Petros and Ulmsten, "Pregnancy Effects on the Intravaginal Sling Operation," Acta Obstet. Gynecol. Scand., 1990, 69 (Suppl. 153):77-78.

Petros and Ulmsten, "The Combined Intravaginal Sling and Tuck Operation. An Ambulatory Procedure for Cure of Stress and Urge Incontinence," Acta Obstet. Gynecol. Scand., 1990, 69(Suppl. 153):53-59.

Petros and Ulmsten, "The Development of the Intravaginal Slingplasty Procedure: IVS II—(with bilateral "tucks")," Scand. J. Urol. Nephrol., 1993, Suppl. 153:61-67.

Petros and Ulmsten, "The Free Graft Procedure for Cure of the Tethered Vagina Syndrome," Scand. J. Urol. Nephrol., 1993, Suppl. 153:85-87.

Petros and Ulmsten, "The Further Development of the Intravaginal Slingplasty Procedure: IVS IV—(with "double-breasted" unattached vaginal flap repair and "free" vaginal tapes)," Scand. J. Urol. Nephrol., 1993, Suppl. 153:73-79.

Petros and Ulmsten, "The Intravaginal Slingplasty Procedure: IVS VI—further development of the "double-breasted" vaginal flap repair—attached flap," Scand. J. Urol. Nephrol., 1993, Suppl. 153:81-84.

Petros and Ulmsten, "The Posterior Fornix Syndrome: A Multiple Symptom Complex of Pelvin Pain and Abnormal Urinary Symptoms Deriving from Laxity in the Posterior Fornix of Vagina," Scand. J. Urol. Nephrol., 1993, Suppl. 153:89-93.

Petros and Ulmsten, "The Role of a Lax Posterior Vaginal Fornix in the Causation of Stress and Urgency Symptoms: a Preliminary Report," Acta Obstet. Gynecol. Scand., 1990, 69(Suppl. 153):71-73.

Petros and Ulmsten, "The Tethered Vagina Syndrome, Post Surgical Incontinence and I-Plasty Operation for Cure," Acta Obstet. Gynecol Scand., 1990, 69(Suppl.153):63-67.

Petros and Ulmsten, "The Tuck Procedure: A Simplified Vaginal Repair for Treatment of Female Urinary Incontinence," Acta Obstet. Gynecol. Scand., 1990, 69(Suppl.153):41-42.

Petros and Ulmsten, "Urethral Pressure Increase on Effort Originates From Within the Urethra, and Continence From Musculovaginal Closure," Neurourology and Urodynamics, 1995, 14:337-350.

Petros et al., "The Autogenic Ligament Procedure: A Technique for Planned Formation of an Artificial Neo-Ligament," Acta Obstet. Gynecol. Scand., 1990, 69(Suppl. 153):43-51.

Petros, "Development of Generic Models for Ambulatory Vaginal Surgery—a Preliminary Report," Int. Urogynecol. J., 1998, 9:19-27.

Product Monograph for Aris Transobturator Tape for the Treatment of Female Stress Urinary Incontinence.

Rackley et al., "Tension-free Vaginal Tape and Percutaneous Vaginal Tape Sling Procedures," Techniques in Urology, 2001, 7(2):90-100.

Rackley, "Synthetic slings: Five steps for successful placement—Follow these steps to insert Transvaginal/Percutaneous slings using vaginal approach alone," Urology Times, 2000, 28:46-49.

Raz et al., "Urological Neurology and Urodynamics," J. Urol., 1992, 148:845-850.

Raz, "Modified Bladder Neck Suspension for Female Stress Incontinence," Urology, 1981, 17(1):82-85.

Richardson et al., "Delayed Reaction to the Dacron Buttress Used in Urethropexy," J. Reproductive Med., 1984, 29(9):689-692.

Ridley, "Appraisal of the Goebell-Frangenheim-Stoeckel sling procedure," Am. J. Obstet. Gynecol., 1966, 95(5):714-721.

Schumpelick, V. et at., "Minimized polypropylene mesh for preperitoneal net plasty (PNP) of incisional hernias," Chirurg 70:422-430 (1999).

Shaw, W., "An Operation for the Treatment of Stress Incontinence," Br. Med. J. 1949:1070-1073.

Sheiner et al., "An unusual complication of obturator foramen arterial bypass," J. Cardiovasc. Surg., 1969, 10(4):324-328.

Sirls and Leach, "Use of Fascia Lata for Pubovaginal Sling," Female Urology, 1996, Raz (ed.). W.B. Saunders Company, Chapter 32, pp. 376-381.

Sloan and Barwin, "Stress Incontinence of Urine: A Retrospective Study of the Complications and Late Results of Simple Suprapubic Suburethral Fascial Slings," J. Urol., 1973, 110:533-536.

Spencer et al., "A Comparison of Endoscopic Suspension of the Vesical Neck with Suprapubic Vesicourethropexy for Treatment of Stress Urinary Incontinence," J. Urol., 1987, 137:411-415.

International Search Report and Written Opinion issued in PCT/GB2004/001390, mailed Sep. 3, 2004, 12 pages.

* cited by examiner

METHOD FOR SOFT TISSUE ANCHORING WITH INTRODUCER

CROSS-REFERENCE TO RELATED APPLICATIONS

This application is a continuation of pending U.S. application Ser. No. 12/837,601 filed Jul. 16, 2010 and entitled APPARATUS AND METHOD FOR TREATING FEMALE URINARY INCONTINENCE, which is a continuation of U.S. application Ser. No. 11/199,061 filed Aug. 8, 2005, now U.S. Pat. No. 7,789,821, which in turn is a continuation of U.S. application Ser. No. 10/398,992, filed Apr. 11, 2003, now U.S. Pat. No. 6,960,160, which in turn is a national stage application under 35 U.S.C. 371 of International Application No. PCT/GB01/04554, filed Oct. 12, 2001, which in turn claims priority of Great Britain Application No. GB0025068.8, filed Oct. 12, 2000, the contents of each of which are incorporated by reference herein for all purposes.

This invention relates to an apparatus and method for treating female urinary incontinence and, in particular, to a surgical implant having a sling that passes under the urethra in use and supports the urethra to alleviate incontinence, along with related apparatus and methods for inserting the surgical implant in the body.

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey-type endoscopic procedures in which the sutures are placed so as to elevate the bladder neck.

This invention is particularly directed to improvement of a known procedure in which a sling is positioned loosely under the urethra, commonly known as TVT (tension free vaginal tape) and described, for example, in international Patent Applications No. WO97/13465 and WO97/06567. It is generally understood that this treatment alleviates urinary incontinence by occluding the mid-urethra (for example at a time of raised abdominal pressure by coughing or the like).

The sling is provided in the body using two large curved needles which are provided at each end of the sling, which sling comprises a long mesh or tape. Each of the needles is carried on an insertion tool (which is basically a handle facilitating manipulation of the needles). The mesh or tape is usually made of knitted polypropylene (such as Prolene®). The mesh or tape is generally covered with a plastics sleeve or polyethene envelope to aid smooth insertion, the mesh or tape having rough surfaces to aid retention in the body.

An incision is made in the anterior vaginal wall and the first of the needles is passed through the incision, past one side of the urethra, behind the pubic bone, through the rectus sheath and out through the lower anterior abdominal wall. Likewise, the second needle is passed through the incision, past the other side of the urethra, behind the pubic bone, through the rectus sheath and out through the lower abdominal wall. The needles are separated from their respective insertion tools and also from the mesh or tape such that only the tape and its plastics sleeve are left in the body, passing from a first exit point in the lower abdominal wall, through the rectus sheath, behind the pubic bone, under the urethra, back behind the pubic bone, back through the rectus sheath and out through a second exit point in the lower abdominal wall.

The plastics sleeve is then removed from the tape and the tape adjusted to a suitable tension (such that the tape provides a sling that passes loosely under the urethra, as described above) by maneuvering the free ends of the tape outside the exit points in the lower abdominal wall whilst the urethra is held using a rigid catheter inserted therein. The tape is then cut such that it just falls short of protruding from the exit points in the lower abdominal wall. The exit points and the incision in the upper vaginal wall are then closed by sutures. The tape is held in position by virtue of friction between the tape's rough edges and the surrounding body tissue (such as the rectus sheath and the body tissue behind the pubic bone) and subsequent natural adhesion of the tape with the body tissue as it re-grows around the mesh material. Whilst highly effective in treating urinary incontinence, this procedure has a number of problems. One such problem is that the needles used for inserting the tape are comparatively large, with the needles having, for example, a diameter of around 5-6 mm and a length of around 200 mm. As well as causing concern for patients viewing such needles before or during the procedure (which is carried out under local anaesthetic), this can also lead to a high vascular injury rate.

Similarly, the requirement that the needles exit the lower abdominal wall is disadvantageous due to the trauma to the patient in this area and pain of such abdominal wounds. A further disadvantage is that the tape comprises a relatively large foreign body mass to be retained within the patient and this can lead to related inflammation, infection translocation, erosion, fistula and such like.

Similarly, the nature of the large needles and tape, along with the tools required to insert these in the body, lead to the procedure having a relatively high cost.

According to a first aspect of the present invention there is provided a surgical implant for supporting the urethra, the implant comprising: a suburethral support suspended between at least two soft tissue anchors attached at either side of the suburethral support, each soft tissue anchor having retaining means for retaining each anchor in tissue and suspending means for suspending each side of the suburethral support from a soft tissue anchor such that the suburethral support passes under the urethra in use.

Preferably the retaining means of the soft tissue anchor is capable of being inserted into soft tissue or fascia from an incision in the upper vaginal wall without the need to penetrate the lower abdominal wall.

In one embodiment the soft tissue anchor is insertable into the rectus sheath of the human or animal body to anchor suspending means to the soft tissue, the suspending means being attached to the soft tissue anchor and the soft tissue anchor having retaining means adapted to prevent retraction of the anchor from the rectus sheath in a direction opposite to that of insertion of the anchor into the tissue.

Preferably the soft tissue anchor comprises a central portion and the retaining means includes at least one wing section, the wing section being mounted on a first end of the central portion by resilient hinge means such that the wing section is moveable between an open, resting position and a deflected position such that in use, when the soft tissue anchor device is inserted into the tissue the wing section is pushed or held towards the central portion to a deflected position to permit entry of the soft tissue anchor into the tissue and through the rectus sheath, wherein the wing section returns to its open or resting position and prevents the soft tissue being removed.

Preferably the resilient hinge means allows the wing section to return to its resting position from its deflected position following penetration of the soft tissue anchor through the rectus sheath such that the wings of the soft tissue anchor once pushed through the rectus sheath can rest on the surface of the rectus sheath fascia opposite to the surface through which the soft tissue anchor is inserted and thus the soft tissue anchor cannot be retracted.

Preferably the resilient hinge means is capable of preventing the wing section being moved to a position greater than substantially perpendicular to the central portion.

Preferably the central portion of the soft tissue anchor comprises a hollow passage which extends from a first end of the central portion to a second opposite end of the central portion.

Preferably an introducing tool can be placed into the hollow passage such that the introducing tool extends through the central portion the soft tissue anchor such that the introducing tool extends to a point beyond the first end of the central portion.

Preferably the soft tissue anchor comprises a plurality of wing sections.

More preferably the soft tissue anchor comprises four wing sections arranged radially around the first end of the central portion.

Preferably the soft tissue anchor in addition to comprising a central portion and a wing section also comprises at least one stud element arranged radially around the first end of the central portion, the stud having an inclined face in the opposite direction to that in which the soft tissue anchor is inserted to aid separation of the tissue during entry of the soft tissue anchor enabling easier passage of the soft tissue anchor through the soft tissue.

Preferably the soft tissue anchor does not comprise a sharp point.

In an alternative embodiment the soft tissue anchor is capable of anchoring in the retropubic tissue space without penetrating the rectus sheath.

Preferably the soft tissue anchor in this embodiment permits fixation at multiple points via a christmas tree type configuration of deflectable wings.

A soft tissue anchor according to this embodiment comprises a central portion and the retaining means includes a plurality of projections the projections extending radially from the central portion along a substantial portion of the length of the central portion allowing fixation at a plurality of layers. Preferably the projections extend radially from the central portion at an angle inclined toward the second end of the central portion.

Preferably the projections are of a shape that they are able to provide additive traction to the soft tissue anchor and allow it to grip fibro-fatty soft tissue and blood vessels of the paraurethral tunnel below the level of the rectus sheath.

In yet a further embodiment the soft tissue anchor may comprise a substantially flat head the bottom surface nearest the suspending means of the flat head providing the retaining means which, in use is held in the rectus sheath.

In a further embodiment the soft tissue anchor may comprise a sharp point allowing it to pierce or penetrate the rectus sheath, and retaining means comprising a surface or protrusion directed rearwardly with respect to the sharp point which does not cause the soft tissue to part and thus prevents the soft tissue anchor from being pulled back out through the rectus sheath soft tissue in the direction opposite to that in which it is inserted into the soft tissue.

Preferably the sharp point is provided by the apex of a conical head portion and retaining means are provided by a substantially flat base of the conical head.

In any embodiment the soft tissue anchor is comprised of plastics material.

Typically the soft tissue anchor is comprised of polypropylene.

Alternatively the soft tissue anchor is comprised of absorbable material so as to form temporary fixation in soft tissue.

The soft tissue anchor may comprise a point formed of absorbable material including polyglactin, the sharp point thus capable of facilitating insertion of the anchor, yet being absorbed by the body later.

Preferably the soft tissue anchor may be integral with the suspending means.

More preferably the soft tissue anchor is integrally formed from polypropylene or other polymeric material the attachment between the anchor and the suspending being formed as a single unit.

An integral construction of the soft tissue anchor and suspending means has the advantage of simplifying the construction of the soft tissue anchor and suspending means, which can reduce the possibility of defective manufacture etc. and reduce costs and the chance of the soft tissue anchor and suspending means becoming detached once implanted in the body.

Alternatively the soft tissue anchor is attached to the suspending means by a thin metal tube crimped or otherwise attached around the suspending means and central portion of the soft tissue anchor.

The suburethral support of the first aspect of the invention passes under the urethra, loosely supporting the urethra, the suburethral support being held in position by suspending means attached to each of its free ends on either side of the urethra, the suspending means being attached at the opposite end to at least one soft tissue anchor.

Preferably the suburethral support is comprised of flat polymer tape.

Preferably the suburethral support has dimensions sufficient only to pass around the urethra.

More preferably the suburethral support has dimensions of length 15-35 mm, width 5-15 mm and thickness 50-350 µm.

In one embodiment the suburethral support has dimensions of length 25 mm, width 10 mm and thickness 100 µm.

Preferably the suburethral support has at least two junctions to attach the suburethral support to the suspending means.

One problem with the preferred arrangement of a soft tissue anchor and suspending means for suspending the suburethral support of the surgical implant of the invention is that it is difficult to predetermine what length the suspending means must be to position the suburethral support loosely under the urethra as desired.

This is because the distance between the rectus sheath in which the soft tissue anchor is inserted and the urethra varies from patient to patient.

Preferably the distance between the soft tissue anchor(s) and the suburethral support is adjustable.

More preferably the soft tissue anchor (or anchors) can be positioned first and the suburethral support then positioned by adjusting the length of the suspending means.

Preferably the suburethral support is provided with at least one attachment tab to which suspending means are releasably or permanently attached.

Preferably the suburethral support comprises an attachment tab comprising a tunnelled element and an aperture, the tunnelled element being located at each of the free ends of the suburethral support on either side of the urethra at a position that the suspending means are capable of being introduced through, the tunnelled element co-operating with the aperture such that suspending means can be passed through the tunnelled element and then through the aperture, the aperture being present on the opposite surface of the suburethral support to that which contacts the urethra the aperture having an edge capable of co-operating with a ring element and the ring element being capable of being fitted around the aperture trapping the suspending means between the ring element and the edge of the aperture such that the suspending means remain fixed in an adjusted position wherein the suburethra support hanging loosely under the urethra.

Alternatively the attachment tab comprises at least one slot through which suspending means can be passed, the suspending means being permanently attached to the slot by tying.

Alternatively the attachment tab comprises jamming slots that the suspending means can be permanently attached by being threaded through the jamming slots such that the suspending means are held in an adjusted position.

Alternatively the suburethral support is capable of being suitably positioned under the urethra by altering the position of the soft tissue anchors within the body such that at least one soft tissue anchor is secured in the soft tissue or in the rectus sheath and a subsequent anchor is inserted into the soft tissue or rectus sheath to a suitable depth such that the suburethral support hangs loosely under the urethra.

Alternatively the suspending means may be attached to the suburethral support by healing such that the suburethra support and/or suspending means melt and form a join.

Alternatively the attachment tabs may have closure means for gripping the suspending means.

The suspending means may be any means suitable for connecting each end of the suburethra support to the soft tissue anchor (or respective soft tissue anchors).

Preferably the suspending means comprises a plastics strip.

Preferably the plastics strip has smooth edges.

Preferably the plastics strip comprises material such as polypropylene or other suitable non-absorbable or absorbable polymer tape.

Preferably the plastics strip is 3-5 mm in width.

Preferably the plastics material comprises pores which extend through the plastics material from a first surface of the plastics material to a second opposite surface of the plastics material said pores ranging in width across the surface of the plastics material from 50 µm to 200 µm, the pores allowing tissue in-growth to secure the strip in the body.

Alternatively the plastics material may comprise pits, that indent but do not extend through the plastics material, on at least one of the surfaces of the plastics material, the pits ranging in width from 50 µm to 200 µm, the pits allowing tissue in-growth to secure the strip in the body.

Preferably the plastics material comprises pits or pores ranging in width across the surface of the plastics material from 100 µm to 150 µm.

Preferably the pits or pores are distributed across the complete surface of the plastics material.

Alternatively the pits or pores are distributed only in a particular portion of the surface of the plastics material.

Preferably the pits or pores are created by post synthesis modification of the plastics material.

More preferably the pits or pores are created by post synthesis treatment of the plastics material by a laser.

Alternatively the pits or pores of between 50-200 µm are created during synthesis of the plastics material by spaces between the waft and weave of mono-filament or multi-filament yarns when the filaments are woven to form a mesh.

Alternatively pits or pores formed during the synthesis of plastics material are formed by the inter-filament spaces created when mono-filaments are twisted to create multi-filaments, the multi-filaments then being woven to form a mesh.

In an embodiment the suspending means is provided with a plurality of microgrooves width between 0.5-7 µm and of depth 0.25-7 µm on at least one surface of the plastics strip.

Preferably the microgrooves are 5 µm in width and 5 µm in depth.

Preferably the plurality of microgrooves are aligned such that they are substantially parallel with each other.

Preferably the plurality of microgrooves are aligned such that they are separated by ridges which range in size between 1-5 µm in width.

More preferably the microgrooves are separated by ridges of 5 µm in width.

Preferably the ridges are formed by square pillars and the base of the microgroove is substantially perpendicular to the square pillars.

Alternatively the ridges are formed by square pillars and the base of the microgroove is bevelled in relation to the pillars.

Preferably the microgrooves are present on at least one surface of the suspending means.

More preferably the microgrooves are present on a plurality of surfaces of the suspending means.

These microgrooves act to orientate and align the proliferating fibroblasts on the surface of the plastics material and cause axial alignment of collagen fibres and formation of at least one strong ordered neoligament.

The orientation and alignment of the proliferating cells is capable of adding mechanical strength to the tissue which forms around the plastics material such that it is more able to support the urethra.

Preferably the suburethral support of the present invention has neither pores, pits or grooves to discourage the formation of pen-urethral adhesions.

According to a second aspect of the present invention there is provided a method of supporting the urethra comprising the steps of, introducing a surgical implant as described above into an incision made on the upper wall of the vagina, inserting a soft tissue anchor on a first side of the urethra behind the pubic bone, inserting a second soft tissue anchor on a second side of the urethra behind the pubic bone, such that the suburethral support is suspended from the soft tissue anchor supports the urethra.

The invention also provides the use of the method of supporting the urethra in treating urinary incontinence or uterovaginal prolapse.

In one embodiment of the method the soft tissue anchors are inserted in the rectus sheath.

In an alternative embodiment of the method the soft tissue anchors are inserted in the fibro-fatty soft tissue of the retropubic tissue space and do not penetrate the rectus sheath.

The invention also provides an introducing tool comprising an elongate housing adapted to receive the soft tissue anchor at one end and a point which is capable of extending through the central portion of a soft tissue anchor for use in carrying out the method of the invention such that the introducing tool enables access and placement of the soft tissue anchor through the rectus sheath or in the fibrous fatty soft tissue of the para-urethral tunnel from an insertion point in the upper vaginal wall.

More preferably the elongate housing is curved or bent, preferably through an angle of approximately 30.degree.

It is desirable such that a sharp point of an anchor not is not retained in the body that the soft tissue anchor may be inserted using an introducing tool the introducing tool having a sharp point for penetrating the soft tissue.

Preferably an introducing tool comprises a sharp point for piercing or penetrating soft tissue and carrying means for carrying the soft tissue anchor to insert the anchor into the tissue such that the soft tissue anchor device does not require a sharp head and no sharp point is left in the body.

The overall size of the soft tissue anchor and introducing tool may be significantly smaller than that of the needles of the prior art.

Preferably the introducing tool may have a diameter of around 2 mm to 4 mm.

Preferably if the introducing tool is to be used in co-operation with a soft tissue anchor comprising a plurality of projections extending radially from the central portion along a substantial portion of the length of the central portion of the soft tissue anchor, the introducing tool comprises containment means for radially confining the plurality of projections extending from the central portion of the soft tissue anchor during the insertion of the soft tissue anchor.

Thus, when the soft tissue anchor has been inserted, the tool may release the retaining means around the soft tissue anchor such that the projections which have memory are biased to expand radially and grip the soft tissue.

The reduced size of the introducing tool in comparison to the needles used to introduce devices of the prior art can significantly reduce the vascular injury rate and perceptual problems of the prior art for a patient.

Preferably the introducing tool is able or has means for releasably retaining the soft tissue anchor on the end of the housing.

During the insertion of a surgical implant to support the urethra there is a risk of penetration of the bladder wall by the needles during insertion of the tape.

This is known to be a problem with the TVT procedure described by the prior art where the needles are inserted through an incision in the vagina to thread the tape through the respective punctures in the lower anterior abdominal wall.

Following the TVT procedure of the prior art it is therefore conventional to carry out cystoscopy after the tape has been inserted in the body to determine whether or not the bladder has been perforated. This is painful for the patient and also increases the duration of the operation.

The reduced size of the tools used for inserting the surgical implant of the present invention reduce to some degree the risk of the bladder being perforated during the surgical procedure, however t is nevertheless desirable to reduce the need for cystoscopy.

Accordingly at least a part of the surgical implant of the present invention lay be coated or impregnated with a water soluble dye.

Preferably the soft tissue anchor of the present invention is impregnated with a water soluble dye.

Preferably, the water soluble dye is methylene blue.

It is possible to determine whether or not the bladder of a patient has been perforated by a surgical implant or instrument when inserting the surgical implant of the invention into the body, by expelling a small amount of fluid from the bladder, and determining whether or not this small amount of fluid contains any dissolved dye.

Should the bladder be perforated on insertion and placement of the surgical implant into the body, the dye impregnated into the surgical implant will dissolve in the fluid contained in the bladder and diffuse naturally throughout the fluid.

Thus should dye be present in the fluid, it is very likely that the bladder has been perforated and cystoscopy should be carried out. If there is no dye in the fluid, the bladder has not been perforated and the need for cystoscopy is obviated.

The soft tissue anchors as described in relation to the implant of the present invention are capable of use in a variety of situations.

Accordingly the invention provides soft tissue anchors as described herein.

The invention also provides the use of the soft tissue anchors in hernia repair, face lifts, plastic surgery and cosmetic surgery.

Figure 2A:
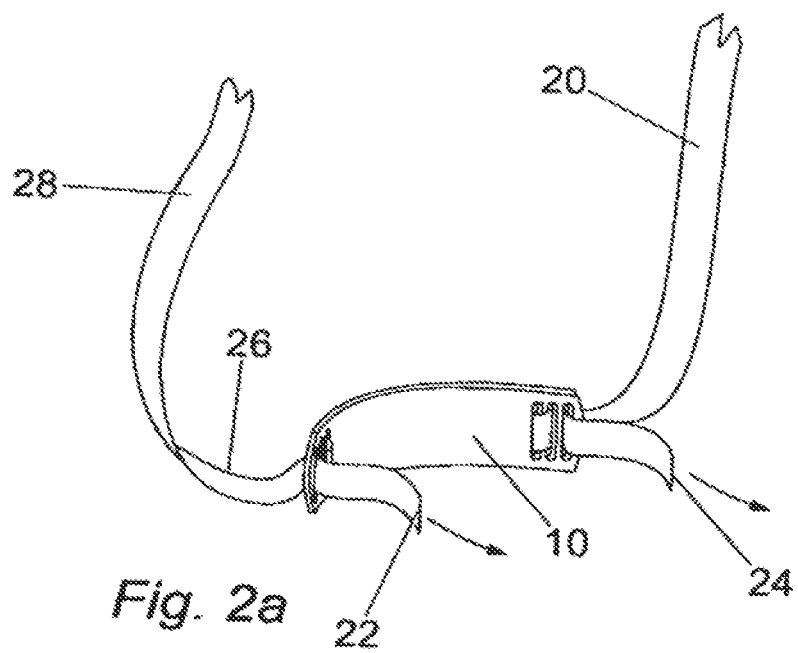
Figure 2B:
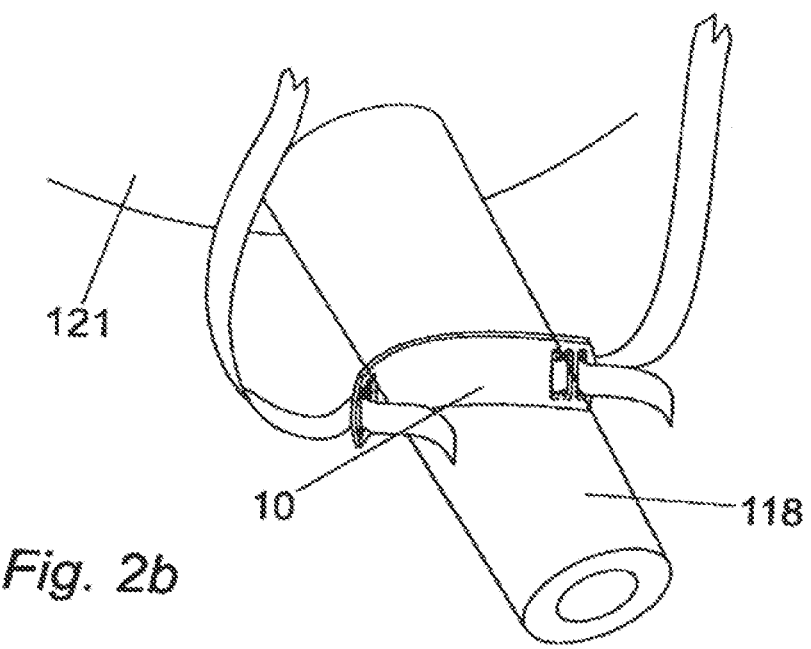
Figure 3:
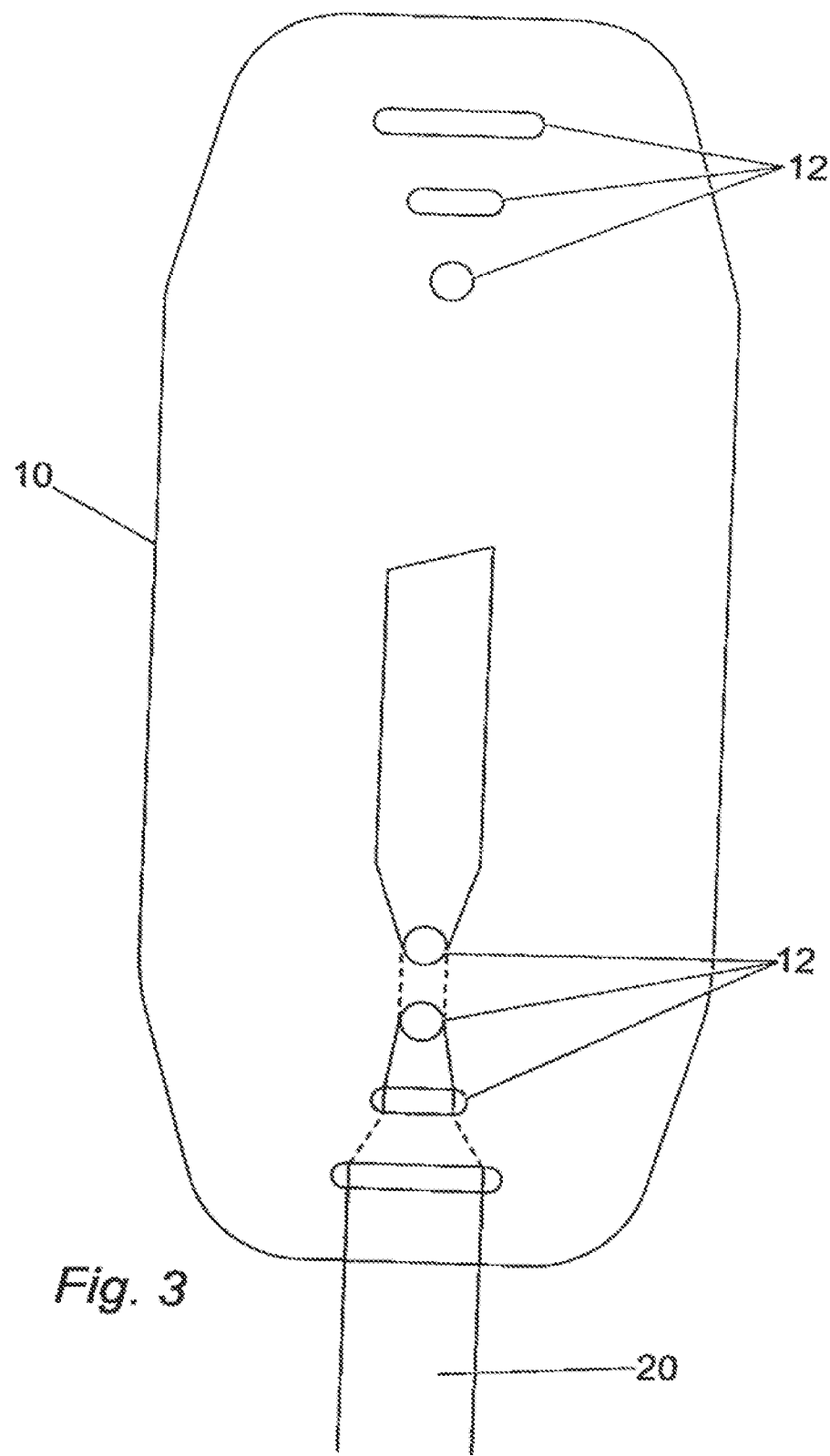
Figure 4:
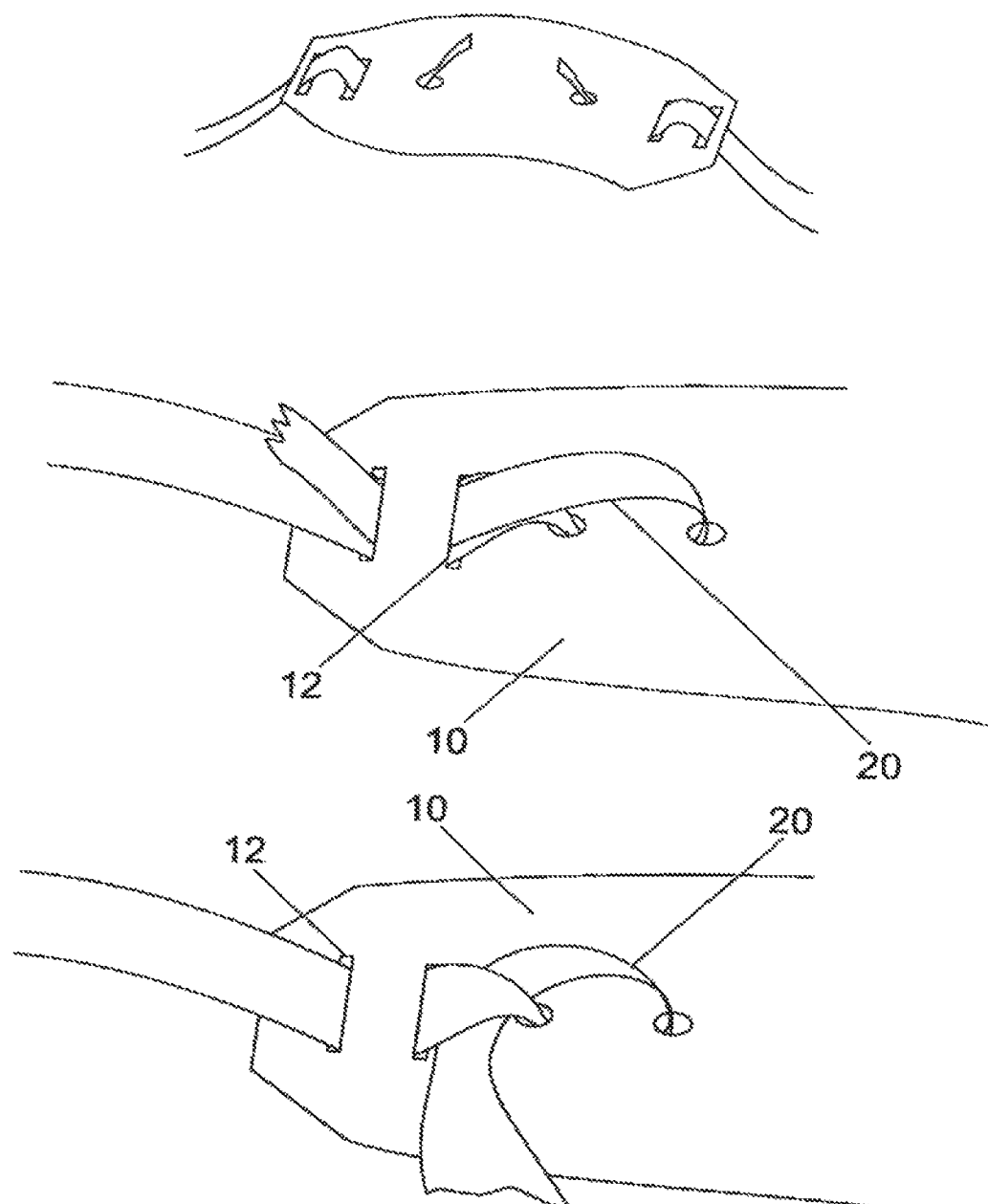
Figure 5:
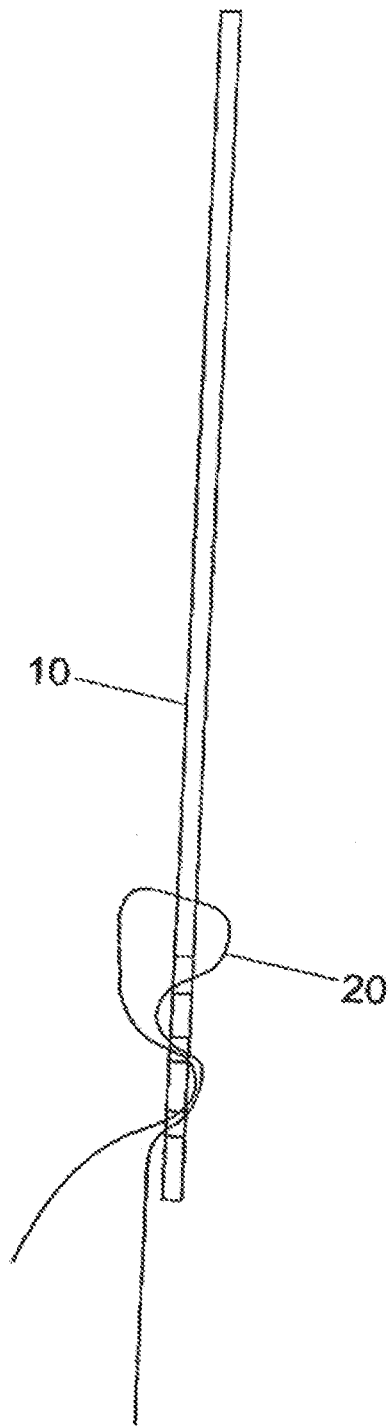
Figure 6A:
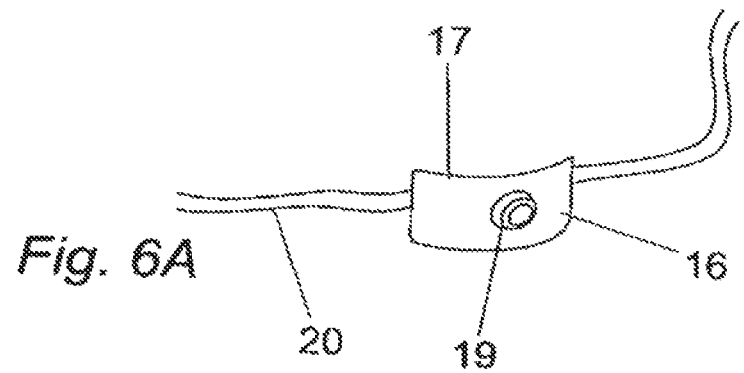
Figure 7A:
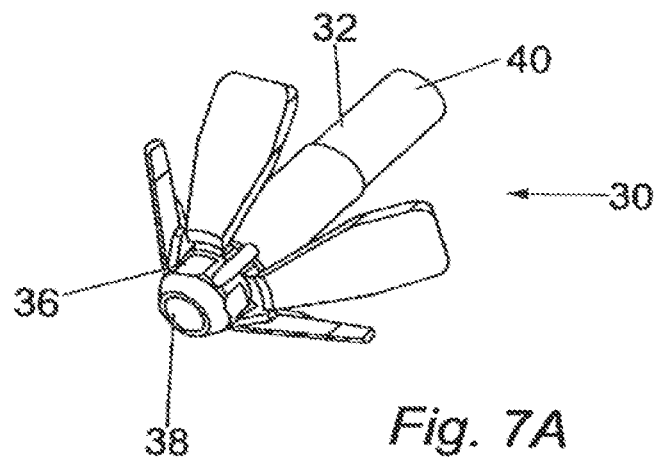
Figure 7B:
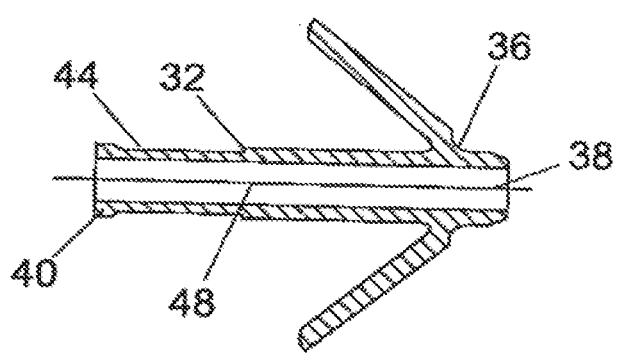
Figure 7C:
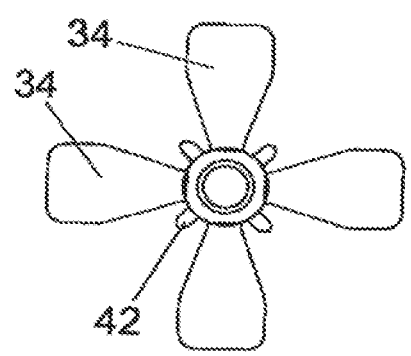
Figure 8A:
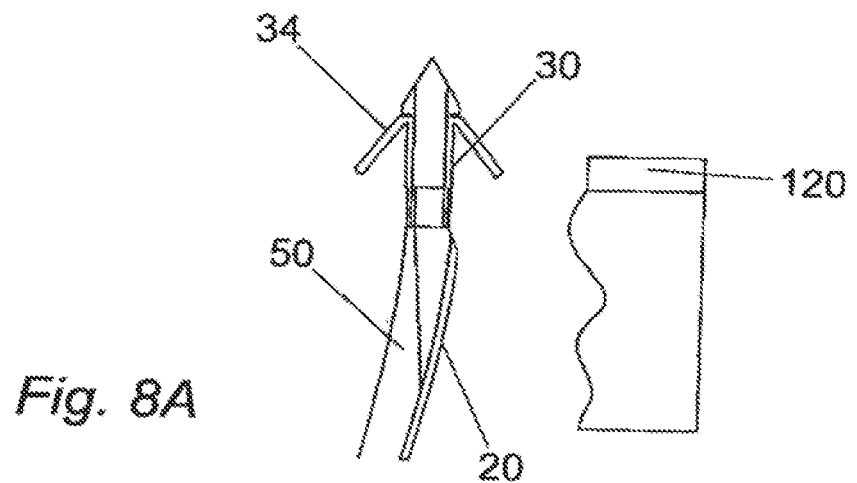
Figure 8B:
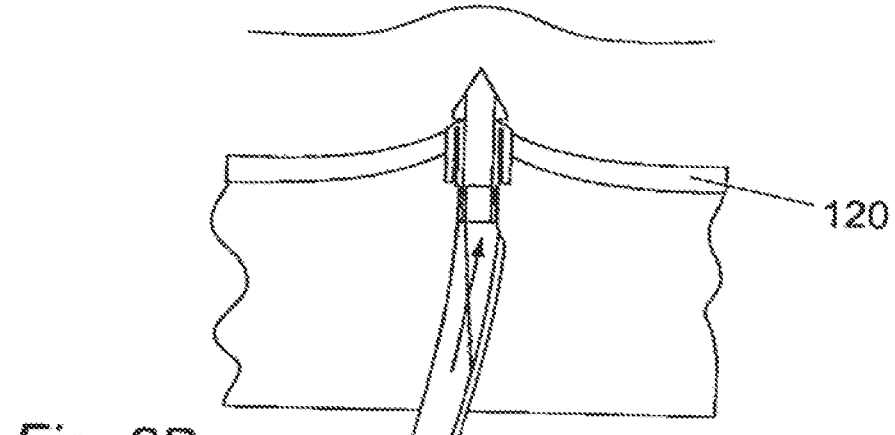
Figure 8C:
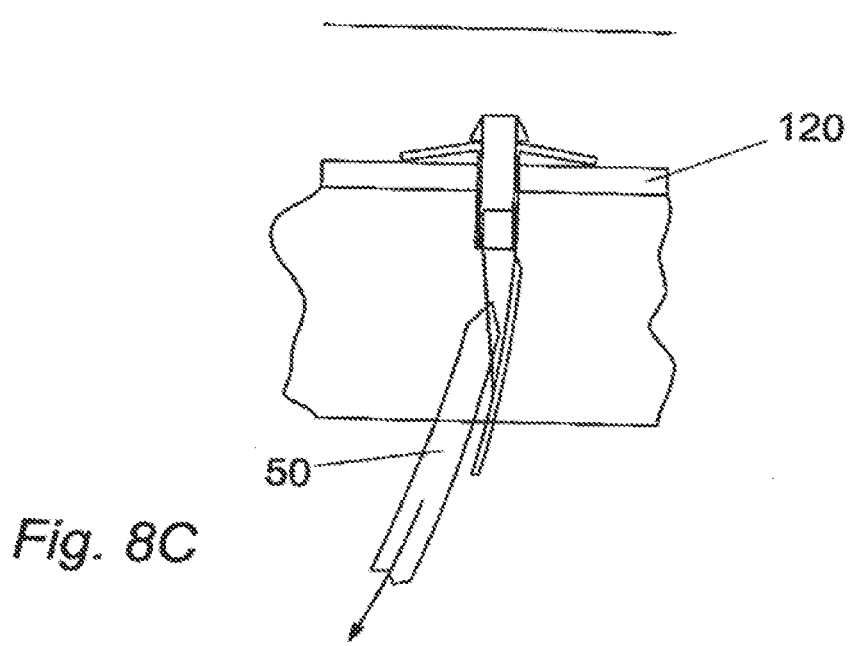
Figure 9:
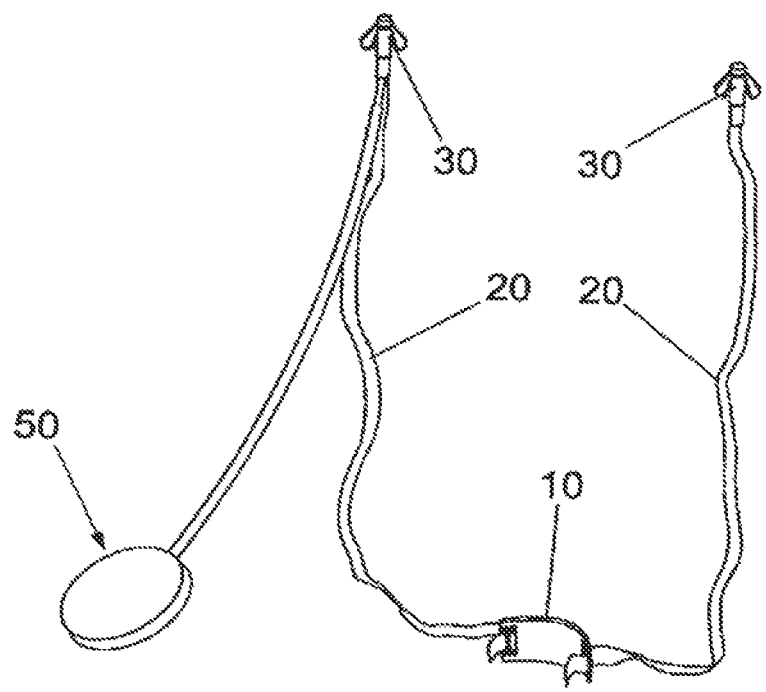
Figure 10:
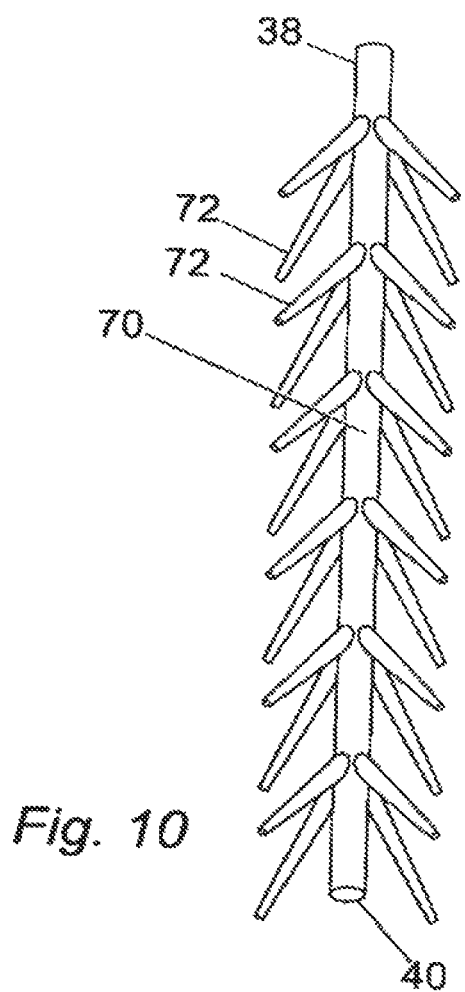
Figure 11:
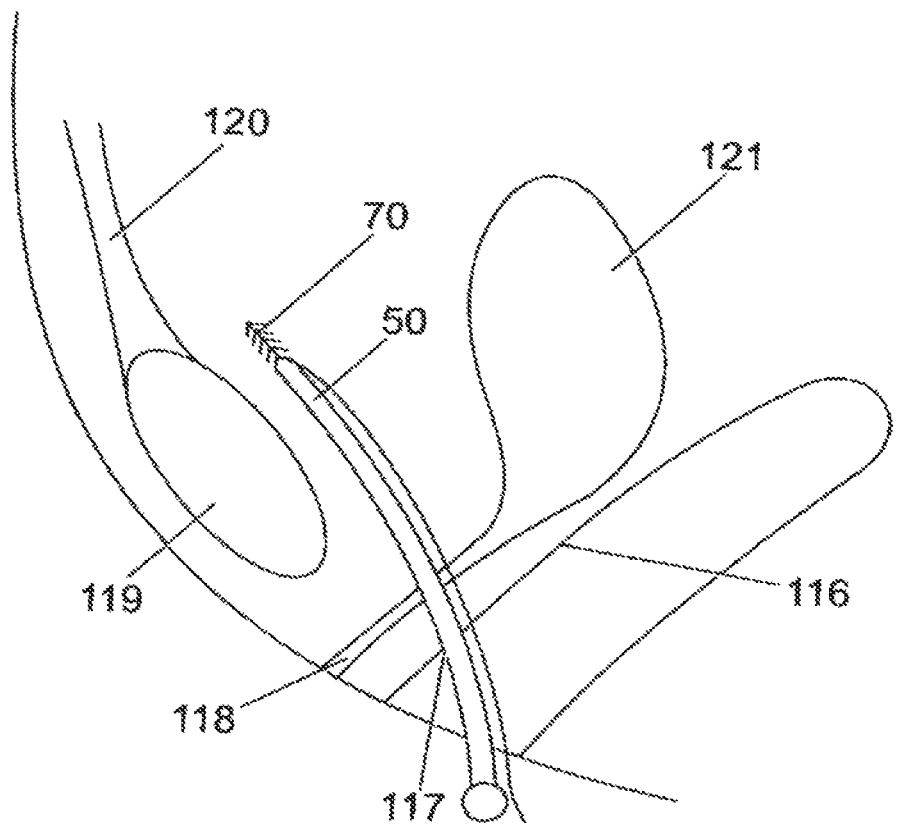
Figure 12:
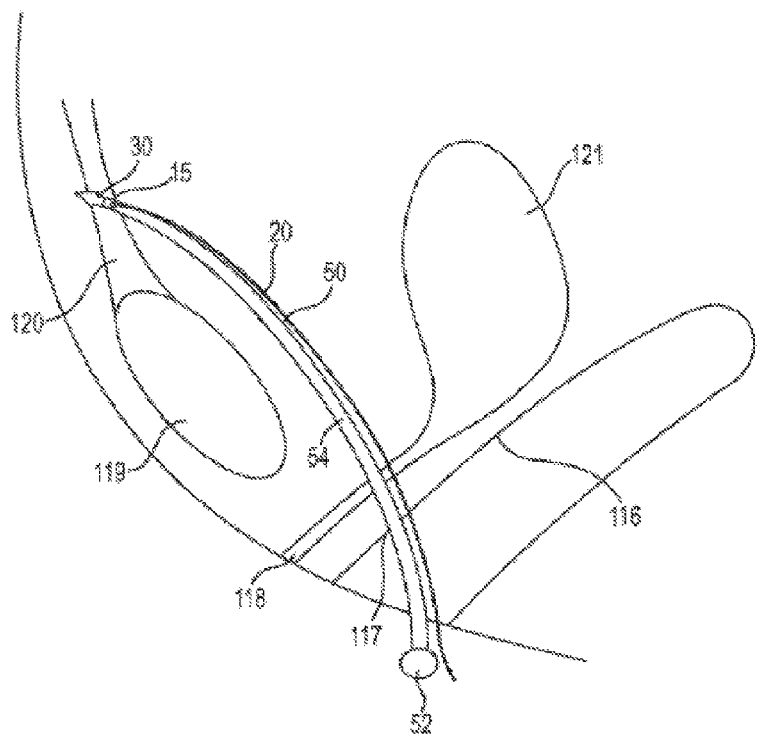
Figure 13:
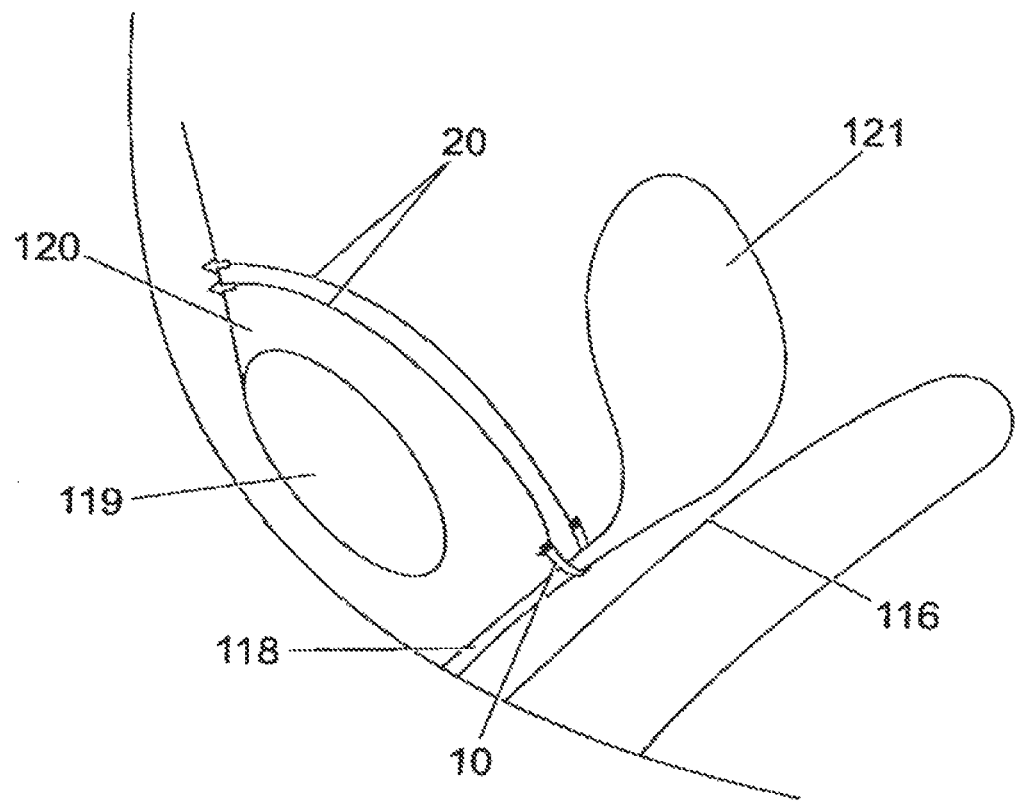
Figure 14:
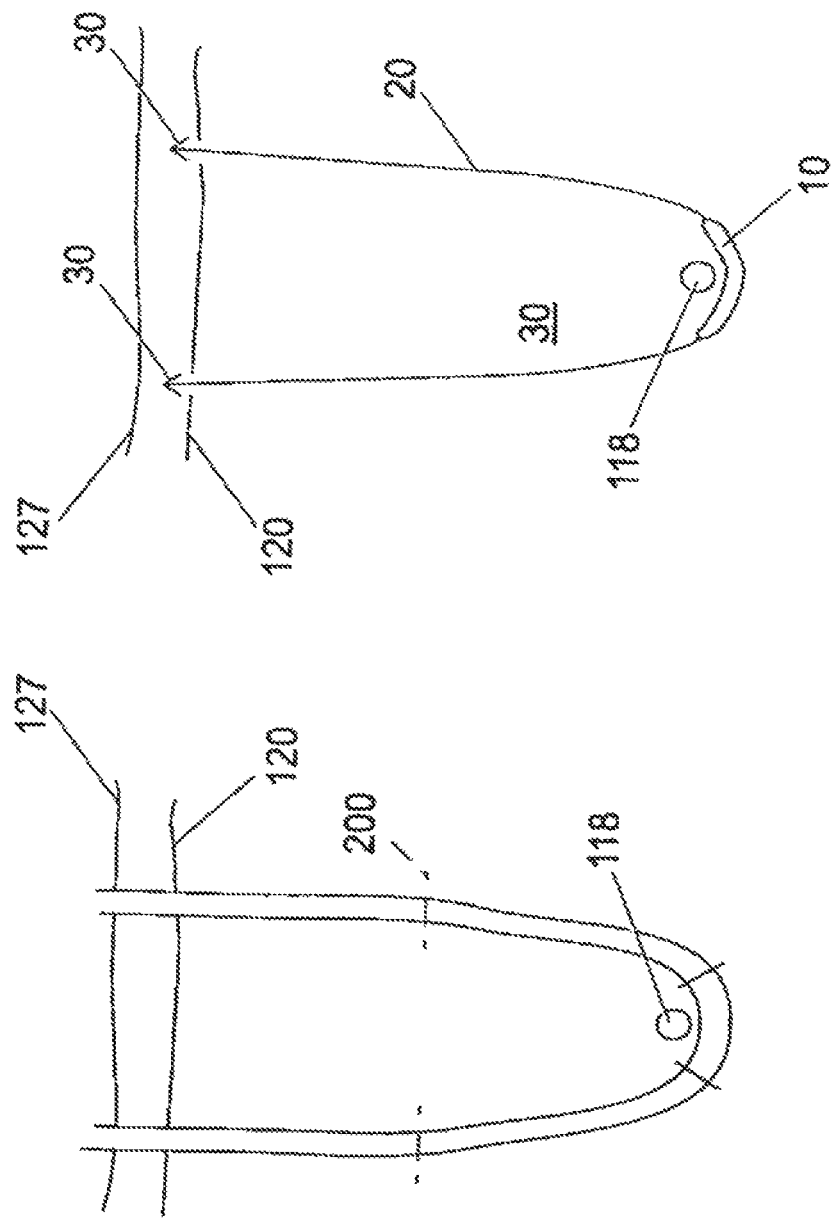
Figure 15:
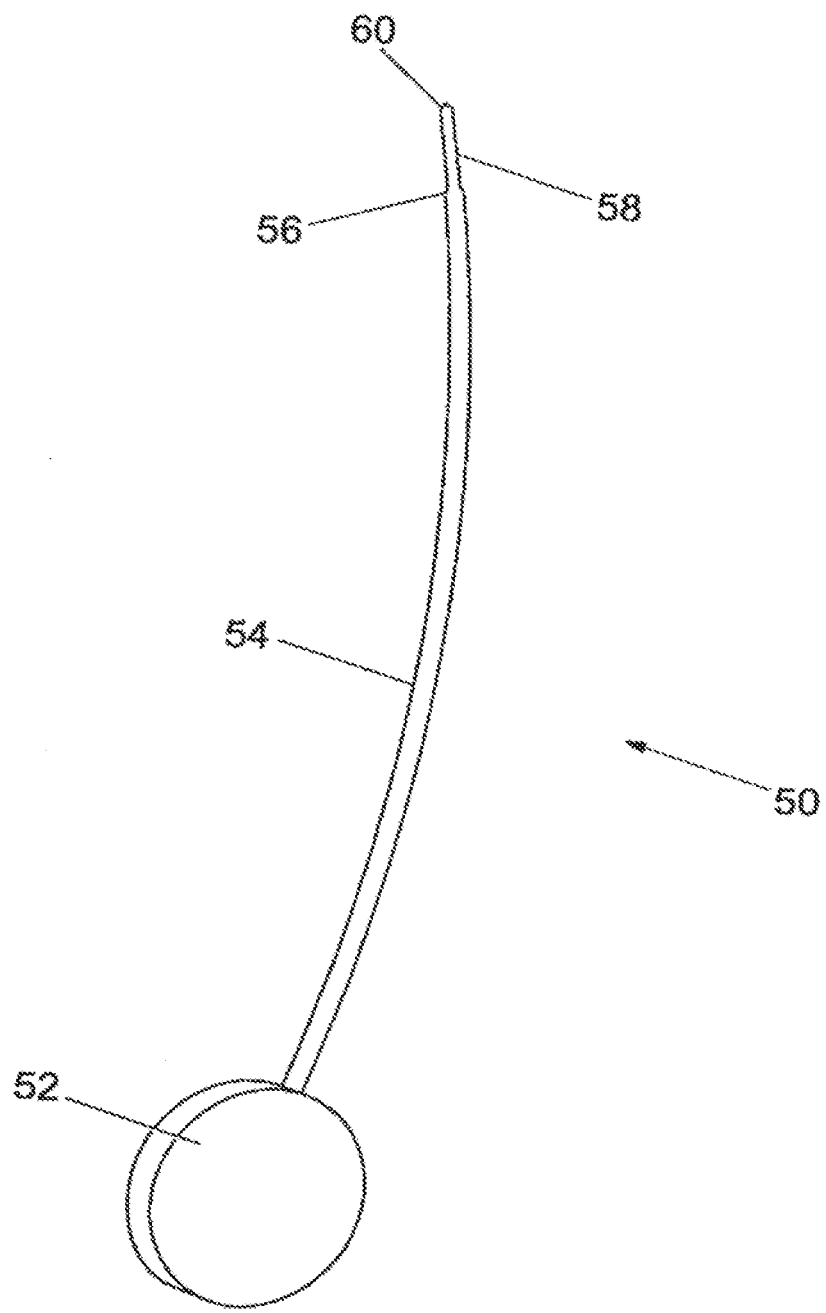
Figure 16:
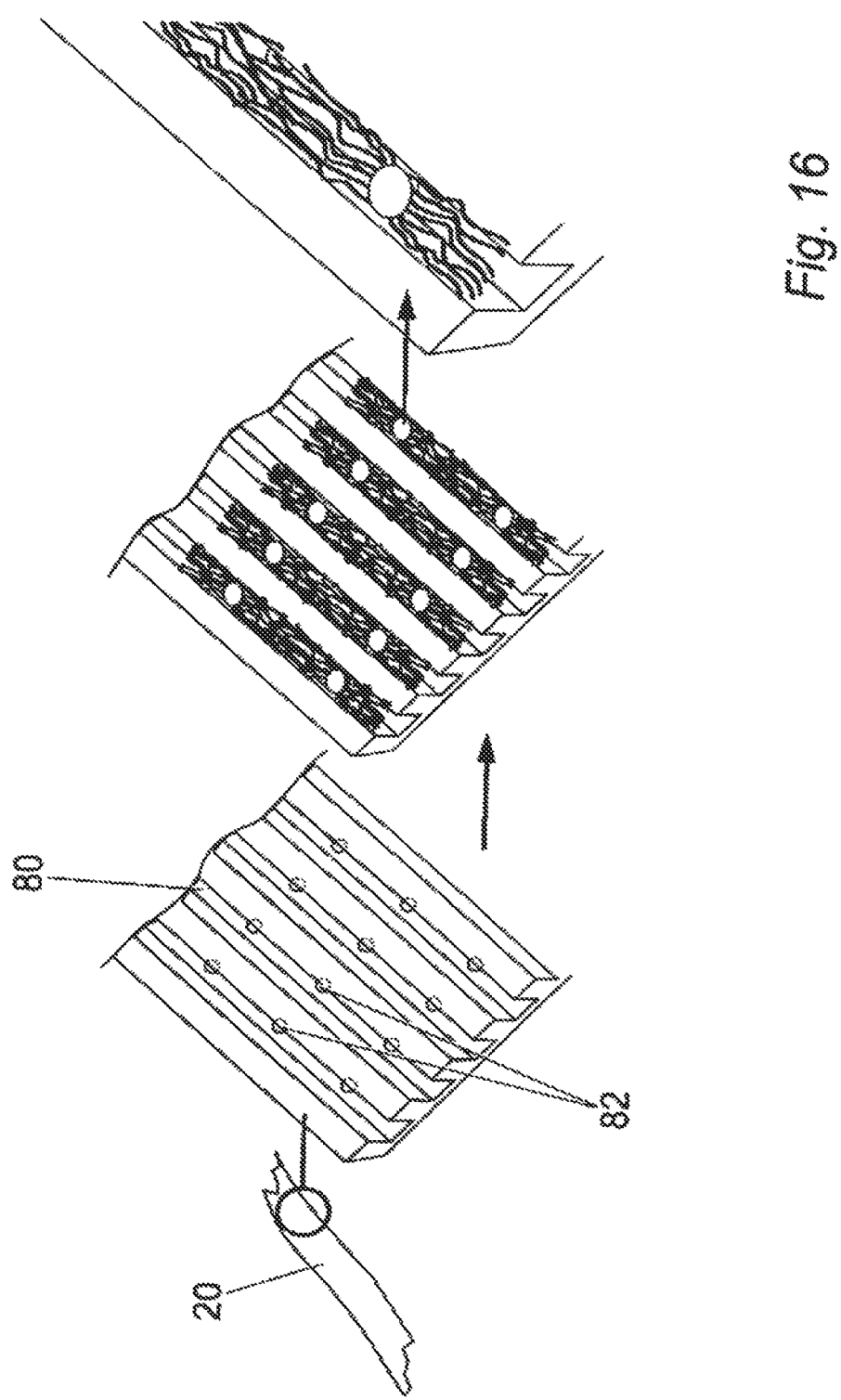

Preferred embodiments of the present invention will now be described, by way of example only, with reference to the accompanying drawings, in which;

FIG. 1 is an illustration of a surgical implant according to the invention,

FIG. 2 is a line drawing of the suspending means attached to the suburethral support, positioned underneath the urethra, FIG. 3 is an illustration of one embodiment of a suburethral support, FIG. 4 is an illustration of a second embodiment of a suburethral support, FIG. 5 shows suspending means being threaded through an attachment tab of a suburethral support, FIGS. 6A, B and C show alternative methods of attaching suspending means to a suburethral support, FIG. 7 is an illustration of a soft tissue anchor for insertion through the rectus sheath, FIGS. 8A-C are sequential illustrations of insertion of a soft tissue anchor of FIG. 7, FIG. 9 is an illustration of a soft tissue anchor mounted on an introducing tool, FIG. 10 is an illustration of a retropubic soft tissue anchor for use in the fibro-fatty tissues of the para-urethral tunnel, FIG. 11 is an illustration of the placement of a soft tissue anchor of FIG. 10, FIG. 12 is an illustration of an implanting tool and a soft tissue anchor inserted into the rectus sheath, FIG. 13 is an illustration of the surgical implant implanted into the rectus sheath, FIG. 14 is an illustration of the prior art contrasted with the technique of the present invention, FIG. 15 is an illustration of the tool used to insert the surgical implant, and FIG. 16 is an illustration of the surface architecture of the suspending means.

Referring to FIG. 1, a surgical implant for treating female urinary incontinence has a suburethral support 10, suspending means 20 and at least two soft tissue anchors 30, the suburethral support 10 being positioned in use, loosely under the urethra. The suburethral support has a length L of around 25 mm and a width W of around 10 mm such that it passes around the urethra with a minimum of excess material, although other similar dimensions would also be suitable. In this example, the suburethral support 10 is made from flat polymer tape. At each side 11,13 of the suburethral support 10 suspending means 20 are provided which attach to the suburethral support 10 at a first end 22,24.

The suspending means 20 are attached at a second end 26 to a respective soft tissue anchor 30.

As shown in FIG. 7 the soft tissue anchor 30 of the embodiment described comprises a central portion 32 and four winged sections 34 which are attached to the central portion at a first end 38 by resilient hinge means 36 and radially extend from the central portion 32 such that when viewed from the front the anchor device resembles a cross.

As shown in FIG. 8A the wing sections 34 of the soft tissue anchor 30 having a resting position in which they are inclined towards the rear 40 of the central portion 32 at an angle of around 45.degree. In FIG. 8B during penetration of the anchor through tissue (the point 60 of the introducing tool enabling the soft tissue anchor to be pushed through the tissue and rectus sheath 120) the wing sections 34 of the soft tissue element 30 may adopt a deflected position which means the penetration of the soft tissue anchor through the tissue and rectus sheath 120 is more effective.

As shown in FIG. 8C once the rectus sheath 120 has been pierced the resilient hinge means 36 cause the wing sections 34 to return to their resting position.

Movement of the soft tissue anchor in a direction opposite to which it was introduced into the soft tissue causes the wing section to be deflected until an endstop 46 is reached which prevents the wing sections 34 moving beyond a point substantially perpendicular to the central portion 32 and prevents retraction of the soft tissue anchor 30 from the soft tissue.

The soft tissue anchor 30 further comprises a hollow portion 48 which extends from the first end 38 to the second rear end 40 of the central portion 32 through which an introducing tool 50 may be placed.

The introducing tool 50 extends through the hollow portion 48 such that it extends as a sharp point 60 from the first end 38 of the soft tissue anchor 30 such that the sharp point 60 allows penetration of the tissue by the soft tissue anchor 30.

Stud like projections 42 which extend radially from the central portion 32 are angled such that they extend further radially from the central portion 32 as they extend towards the rear 40 of the central portion 32, this inclination allowing the soft tissue anchor 30 to pass more easily into the soft tissue.

A recessed portion 44 is positioned toward the rear end 40 of the central portion 32 to facilitate attachment of the suspending means 20 to the soft tissue anchor 30.

The suspending means 30 may be respectively attached to the soft tissue anchor 30 at this recessed point 44 by crimping a tube around the suspending means 20 to fix the suspending means 20 to the soft tissue anchor 30.

In the embodiment shown the soft tissue anchor may be suitably positioned in the rectus sheath 120 using an introducing tool 50. As shown in FIG. 15 the tool 50 comprises a handle 52 and elongate body 54. The elongate body 54 is curved through an angle of approximately 30.degree. to facilitate positioning of the soft tissue anchor 30 in the rectus sheath or surrounding soft tissue of the human body from an incision in the upper wall of the vagina (as described below). The soft tissue anchor 30 is located on the elongate body at a narrowed portion 58 of the introducing tool such that the soft tissue anchor is held in place by an abutment 56 such that the narrowed portion 58 may extend through the hollow portion 48 of the soft tissue anchor 30 such that the point 60 of the insertion tool 50 protrudes from the first end 38 of the soft tissue anchor and allows the soft tissue anchor to be inserted into the human body through the soft tissues and more specifically through the rectus sheath 120 during the placement of the soft tissue anchor.

The placement of the soft tissue anchor 30 on the insertion tool 50 is shown in FIGS. 8B and 8C, which shows the soft tissue anchor 30 being pushed through soft tissue fascia, such as the rectus sheath 120. Once the soft tissue anchor has penetrated the rectus sheath fascia 120, as shown in FIG. 8B, the introducing tool 50 can be withdrawn, as shown in FIG. 80, leaving the soft tissue anchor 30 in place.

As shown in FIG. 9 the soft tissue anchor may alternatively be comprised of a central portion 70 and a plurality of projections 72 the projections extending radially from the central portion 70 and arranged along a substantial portion of the length of the central portion 70. The projections 72 may be of any shape such that they provide resistance within the fibro-fatty soft tissue and blood tissues of the para-urethral tunnel in the direction opposite to that in which the soft tissue anchor is introduced.

This resistance is also provided by the multiple layers, typically between 5-10 layers of projections 72 which extend from the central portion 70.

Using these multiple layers of projections 72 it is not necessary to insert the soft tissue anchor through the rectus sheath 120. Instead the soft tissue anchor should be positioned as high in the retropubic space as possible in the fibro-fatty soft tissue.

In the embodiment of the soft tissue anchor comprising multiple layers of projections 72 which resembles a christmas tree, as shown in FIG. 10, the introducing tool comprises a collar which releasably retains the projections during insertion into the retropubic space. The collar may comprise a semi-sharp bevelled needle. Following insertion of the christmas tree like anchor into the fibro-fatty soft tissue of the retropubic space the introducing tool is withdrawn removing the collar from around the plurality of projections 72 of the soft tissue anchor, which due to their memory expand outwards from the central portion 70 and grip the fibro-fatty soft tissue of the retropubic space at multiple layers. The collar of the introducing tool which extends around the soft tissue may contain a cross-sectional opening such that once the tool is withdrawn the collar may be removed from the surgical implant by passing the implant through the cross-sectional opening.

Accordingly the invention also provides an introducing tool for use in inserting the soft tissue anchor.

Suspending means 20 attached to the soft tissue anchors are formed from a strip of plastics material such as polypropylene which is sufficiently soft to avoid damaging the urethra or surrounding body tissue and suitably inert such that it can be left in the human body for a long period of time without causing adverse reactions. Again, other suitable materials will be apparent to those skilled in the art.

The polypropylene mesh strip of 3-5 mm in width which forms the suspending means 20 has smooth edges to avoid adhesion of the soft tissue to the strip, reducing problems associated with leaving foreign material in the human body for long periods of time. As shown in FIG. 16 the polypropylene mesh strip further comprises pores or pits 80 ranging in width across the surface of the strip from 50 μm to 200 μm, which extend through the strip from a first surface of the strip 26 to a second opposite surface 28 of the strip the pores 80 allowing tissue in-growth to secure the suspending means 20 in the body.

The pores 80 are created by post synthesis treatment of the polypropylene mesh material by a laser.

The polypropylene mesh which forms the suspending means 20 also comprises microgrooves 82 of width 5 μm and of depth 5 μm on the surfaces of the polypropylene mesh.

The microgrooves 82 are aligned such that they are substantially parallel with each other and separated by ridges of around 5 μm in width.

The ridges are formed by square pillars the base of the microgroove being substantially perpendicular to the square pillars or bevelled in relation to the pillars. The microgrooving 82 being present on both surfaces of the suspending means to orientate and align the proliferating fibroblasts on the surface of the plastics material and cause axial alignment of collagen fibres and formation of at least one strong ordered neoligament.

This orientation and alignment of the proliferating cells adding mechanical strength to the tissue which forms around the plastics material such that it is more able to support the urethra.

The suburethral support is not provided with pores, pits or grooves to discourage the formation of peri-urethral adhesions.

Once the soft tissue anchors have been suitably positioned in either the soft tissue of the pare-urethral tunnel or through the rectus sheath 120 the length of the suspending means 20 can be altered such that the suburethral support 10 hangs loosely under the urethra.

As shown in FIG. 2 the suspending means 20 are attached at a first end 22, 24 to the sides 12, 14 of the suburethral support 10, which extend on either side of the urethra.

Figure 6B:
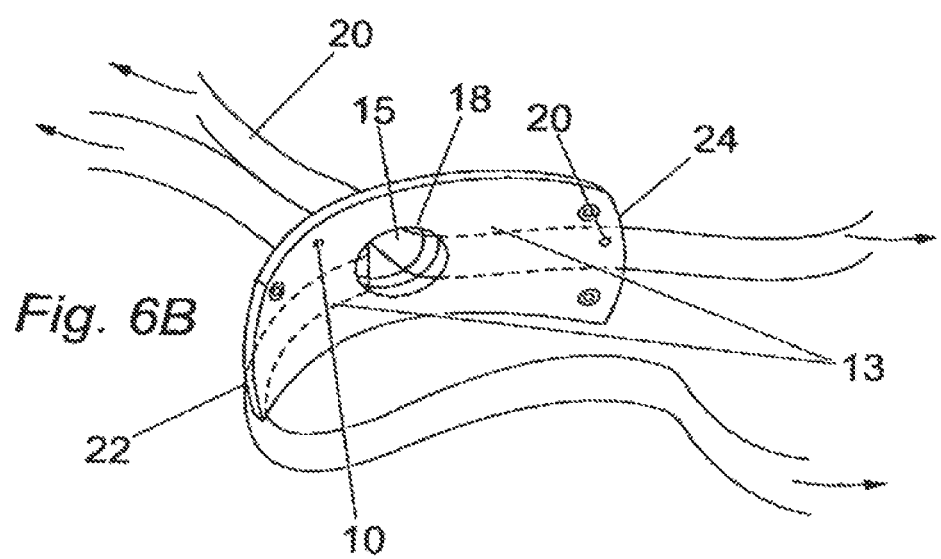
Figure 6C:
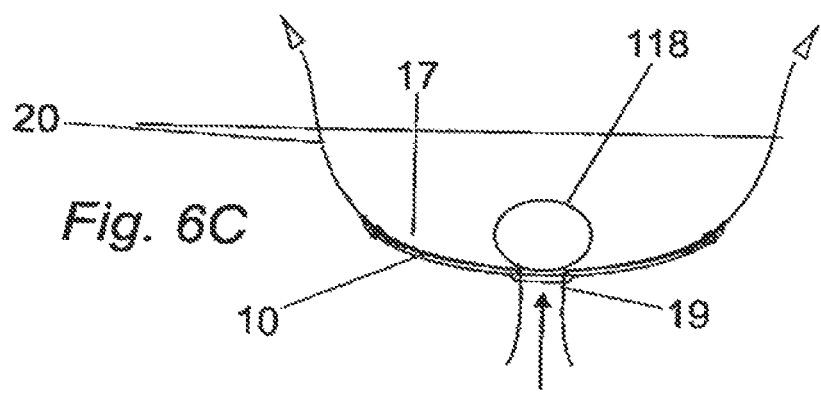

As shown in FIG. 6 a preferred method of altering the length of the suspending means 20 attached to the suburethral support 10 comprises a tunnelled element 13 at each of the free ends 22,24 of the suburethral support 10 on either side of the urethra. The tunnelled element 13 extends from the edges of the suburethral support 10 to an aperture 15, the aperture being present on the opposite surface 16 of the suburethral support 10 to the surface which contacts the urethra 17, the aperture 15 having an edge 18 able to co-operate with a ring element 19 such that the ring element which has memory can be pushed onto the edge 18 of the aperture 15 trapping the suspending means 20 between the edge of the aperture 18 and the ring element 19 thus securing the suburethral support 10 along a particular desired length of the suspending means 20 such that the suburethra support 10 hangs loosely under the urethra.

FIG. 5 shows an alternative method of attaching the suspending means 20 to the suburethral support 10, the suspending means 20 being threaded through jamming slots 12 such that the suspending means 20 are permanently attached to the jamming slots 12 by being pulled into the jamming slots 12 as shown in FIG. 5 such that the suspending means is held tightly in position.

Alternatively as shown in FIG. 6 the suspending means 20 may be passed through slots and the suspending means permanently attached to the slots by tying.

In use, as shown in FIG. 12 the soft tissue anchor 30 is placed on the introducing tool 50 as described above. An incision 117 is made in the upper wall 116 of the vagina, as shown in FIG. 11, and the introducing tool 112 is passed through the incision 117, past one side of the urethra 118, behind the pubic bone 119 and into the rectus sheath 120. It is apparent to the surgeon when the rectus sheath 120 has been penetrated as this stage of insertion presents significant resistance. Once the head 58 of the introducing tool 50 and the soft tissue anchor 30 have passed through the rectus sheath 120, the resistance diminishes and the surgeon ceases to insert the introducing tool 50.

The introducing tool 50 is retracted from the body releasing the soft tissue anchor 30. Due to the wing sections 34 on the central portion 32 of the soft tissue anchor 30, the soft tissue anchor 30 is retained by the rectus sheath 120 as the introducing tool 50 is retracted. Thus, the suspending means remains in the body, secured by the soft tissue anchor which is opposed by the rectus sheath 120.

This procedure is repeated, with a second soft tissue anchor 30 and suspending means 20, with the introducing tool 50 being passed through the incision 117 and past the other side of the urethra 118. Thus, two suspending means 20 are provided, attached to the rectus sheath 120, one passing either side of the urethra 118.

The suspending means 20 are passed through the tunnelled elements 13 of the suburethral support 10, and the suspending means 20 are pulled through the aperture 15 until the suburethral support 10 is positioned such that it passes under the urethra 118. The suspending means 20 are then fixed in place by placing a ring element 19 over the edge 18 of the aperture 15 such that the suspending means are trapped between the edge 18 and the ring element 19 securing them in place.

FIG. 12 is an illustration of an introducing tool 50 and a soft tissue anchor 30 connected to a suspending means 20 (as shown a suture, or filament 20) with the soft tissue anchor 30 inserted into the rectus sheath 120. As shown, the urethra 118 is illustrated relative to the bladder 121 and the incision 117 has been formed in a wall of the vagina 116. The introducing tool 50 has a handle 52 and an elongate body 54. The elongate body 54 has an eye 15, or hole, toward its distal end. The soft tissue anchor 30 is secured to the distal end of the elongate body 54 and the filament 20 extends from the soft tissue anchor 30 with the free end of the filament 20 passed out through the hole 15 formed in the elongate body 54. The free end of the filament 20 is then pulled through the hole 15 until the soft tissue anchor 30 is located at the distal end of the elongate body 54. As shown, the free end of the filament 20 extends alongside the elongate body 54. FIG. 13, in turn, is an illustration of the suburethral support 10 connected to the filament 20 with the soft tissue anchor 30 and the filament 20 released from the introducing tool 50.

Alternatively as shown in FIG. 5 the suspending means may be fixed in the attachment tabs by threading them through jamming slots 12 or tying, as described above. The optimal lengths of the suspending means 20 are such that the suburethral support 10 passes under the urethra 118, but exerts no pressure on the urethra 118 unless the bladder 121 is displaced. The optimal positioning of the suburethral support 20 is roughly as illustrated in FIG. 14. When the bladder is displaced, the suburethral support 10 aids closure of the urethra 118, thus alleviating urinary incontinence.

In this example, a portion of the surgical implant is impregnated with methylene blue, which is a harmless water soluble dye. At the end of the procedure a small amount of fluid is expelled from the bladder 121. Should this fluid contain any dissolved methylene blue, it is very likely that the bladder has been perforated on placing the soft tissue anchor 30. In this case, cystoscopy should be carried out. If no methylene blue is present, the need for cystoscopy is advantageously obviated. Other suitable water-soluble dyes may, of course, be used.

Referring to FIG. 14, it can be appreciated that the surgical implant of the present invention, when inserted in the human body, may extend from the rectus sheath 120, through the paraurethral space 130 on one side of the urethra 118, around the urethra and back to the rectus sheath 120 on the other side. In contrast, the prior art device comprises a tape 200 that also extends through the abdominal wall 127 and represents a far greater implanted mass.

Referring to FIG. 11, in use, the further embodiment of soft tissue anchor illustrated in FIG. 9 for placement in fibro-fatty soft tissue of the retropubic space is placed on an introducing tool. An incision 117 is made in the upper wall 116 of the vagina, as shown in FIG. 11, and the introducing tool 112 is passed through the incision 117, past one side of the urethra 118, and located in the fibro-fatty soft tissue and blood vessels of the para-urethral tunnel. In this case the surgeon does not introduce the soft tissue anchor as far into the body as described previously and the rectus sheath 120 is not penetrated. Once the soft tissue anchor has been suitably positioned in the soft tissue the surgeon ceases to insert the introducing tool and retracts the introducing tool from the body releasing the projections of the soft tissue anchor 72. The release of the projections 72 of soft tissue anchor by the introducing tool allows the projections to grip the soft tissue surrounding the soft tissue anchor and provide resistance to movement of the soft tissue anchor in a direction opposite to that which it was inserted.

This procedure is repeated, with a second soft tissue anchor such that the projections 72 of the soft tissue anchor also provide resistance to movement of the soft tissue anchor in a direction opposite to that which it was inserted the introducing tool being passed through the incision 117 and past the other side of the urethra 118.

Thus, two suspending means 20 are provided, which are held in the soft tissue comprising fibro-fatty tissue and blood vessels.

As described above the suspending means 20 are passed through the attachment tabs of the suburethral support 10, and the suburethral support 10 positioned such that it passes under the urethra 118.

Again this device contrasts that described by the prior art device in that it does not extend through the abdominal wall 127 and does not represent as much implanted mass.

Various embodiments of the present invention can be envisaged within the scope of the invention, for example the soft tissue anchor may comprise a cone or a half cone such that a circular or semi-circular base is provided as a retaining means to prevent retraction of the soft tissue anchor in a direction opposite to that in which it is inserted into the tissue.

Alternatively the soft tissue anchor may comprises a substantially flat or disc shaped head. In this case the introducing tool may have a conical head with a sharp point at its apex and a slot for receiving the flat or disc shaped head.

In yet another example, the soft tissue anchor may be formed of two sections. The upper section, i.e. the portion of the anchor that forms the sharp point 10, may be made from an absorbable material, such as polyglactin such that a sharp point is provided for insertion of the anchor into the body, but this sharp point is later absorbed by the body so as to eliminate any discomfort or disadvantage caused by a sharp pointed object being retained inside the body.

The soft tissue anchor may be made from metal, such as titanium, as this is a hard material that can easily be formed into the head having the sharp point at its apex, and is sufficiently malleable to provide a tube that may be crimped to the suspending means.

What is claimed is:

1. A method of treating urinary incontinence by providing support to a urethra of a patient, the method comprising:
    making a vaginal incision for providing access for placement of a mesh support device below a urethra of a patient without penetrating an abdominal wall of the patient, the mesh support device including a sling portion having a first end and a second end, a first soft tissue anchor connected to the first end, and a second soft tissue anchor connected to the second end;
    delivering the mesh support device through the vaginal incision using an introducer such that the sling portion is suspended from the first and second anchors under the urethra to treat urinary incontinence, the introducer including a curved elongate shaft having a distal portion for connecting with the first anchor and a proximal portion connected to a handle;
    passing a suture coupled to and extending from one of the first soft tissue anchor and the second soft tissue anchor through an aperture in a distal end of the introducer and advancing the introducer over the suture until the first soft tissue anchor or the second soft tissue anchor is located at the distal end of the introducer;
    delivering the first soft tissue anchor into soft tissue on a first side of the urethra and the second soft tissue anchor into soft tissue on a second side of the urethra;
    positioning the sling under the urethra of the patient; and
    suspending the sling from the first and second soft tissue anchors.

2. The method of claim 1, further comprising releasing the first soft tissue anchor from the introducer, wherein the suture remains threaded through the aperture in the distal end of the introducer during withdrawal of the introducer.

3. The method of claim 1, wherein the sling portion has a visual marker indicating a mid-point of the sling portion, the method further comprising positioning the sling portion under the urethra using the visual marker.

4. The method of claim 1, further comprising inserting the first soft tissue anchor into soft tissue along a curved path that is on a first side of the urethra.

5. The method of claim 1, wherein the handle has a first face and a second face opposite the first face, the method further comprising grasping the handle of the introducer and inserting the first soft tissue anchor into the tissue along a curved path that is perpendicular to the first and second faces of the handle.

6. The method of claim 1, wherein the handle has a first face and a second face opposite the first face with an edge between the first and second faces, and the elongate shaft has a curvature in a direction perpendicular to the first and second faces of the handle, the method further comprising inserting the first soft tissue anchor into the tissue with the sling portion positioned along an outer part of the curvature of the introducer.

7. The method of claim 1, further comprising passing the first soft tissue anchor to one side of the urethra, through soft tissues of the perineal space, and behind an inferior pubic ramus of the patient.

8. The method of claim 1, wherein the first soft tissue anchor being delivered through the vaginal incision has a proximal end and a distal end and includes a base, a plurality of barbs, and a tip.

9. The method of claim 1, wherein the sling portion is suspended below a mid-urethra of the patient.

10. The method of claim 1, further comprising suspending the sling portion in a suburethral pressure space below endopelvic fascia of the patient.

11. The method of claim 1, further comprising suspending the sling portion in a perineal space of the patient.

12. A method of treating urinary incontinence by providing support to a urethra of a patient, the method comprising:
    making a vaginal incision for providing access for placement of a mesh support device below a urethra of a patient without penetrating an abdominal wall of the patient, the mesh support device including a sling portion having a first end and a second end, a first soft tissue anchor connected to the first end, and a second soft tissue anchor connected to the second end;
    delivering the mesh support device through the vaginal incision using an introducer such that the sling portion is suspended from the first and second anchors under the urethra to treat urinary incontinence, the introducer including a curved elongate shaft having a distal portion for connecting with the first anchor and a proximal portion connected to a handle;
    passing a filament that extends from and is received by the first soft tissue anchor through an aperture in a distal end of the introducer and advancing the introducer over the filament until the first soft tissue anchor is located at the distal end of the introducer;

delivering the first soft tissue anchor into soft tissue on a first side of the urethra and the second soft tissue anchor into soft tissue on a second side of the urethra;

positioning the sling under the urethra of the patient; and suspending the sling from the first and second soft tissue anchors.

13. A method of treating urinary incontinence by providing support to a urethra of a patient, the method comprising:

making a vaginal incision for providing access for placement of a mesh support device below a urethra of a patient without penetrating an abdominal wall of the patient, the mesh support device including a sling portion having a first end and a second end, a first soft tissue anchor connected to the first end, and a second soft tissue anchor connected to the second end;

delivering the mesh support device through the vaginal incision using an introducer such that the sling portion is suspended from the first and second anchors under the urethra to treat urinary incontinence, the introducer including a curved elongate shaft having a distal portion for connecting with the first anchor and a proximal portion connected to a handle;

passing a suture coupled to and extending from the first soft tissue anchor through an aperture in a distal end of the introducer and advancing the introducer over the suture until the first soft tissue anchor is located at the distal end of the introducer;

delivering the first soft tissue anchor into soft tissue on a first side of the urethra and the second soft tissue anchor into soft tissue on a second side of the urethra;

positioning the sling under the urethra of the patient; and suspending the sling from the first and second soft tissue anchors.

\* \* \* \* \*